United States Patent [19]

Gerlitz et al.

[11] Patent Number: 5,460,953
[45] Date of Patent: Oct. 24, 1995

[54] VECTORS AND COMPOUNDS FOR EXPRESSION OF GLYCOSYLATION MUTANTS OF HUMAN PROTEIN C

[75] Inventors: Bruce E. Gerlitz; Brian W. Grinnell, both of Indianapolis, Ind.

[73] Assignee: Eli Lilly and Company, Indianapolis, Ind.

[21] Appl. No.: 93,217

[22] Filed: Sep. 9, 1993

Related U.S. Application Data

[63] Continuation of Ser. No. 628,063, Dec. 21, 1990, abandoned, which is a continuation-in-part of Ser. No. 484,081, Feb. 23, 1990, abandoned.

[51] Int. Cl.$^6$ .............................. C12N 9/64; C12N 15/57; C12N 15/70; C12N 15/79
[52] U.S. Cl. .................. 435/226; 435/212; 435/69.6; 435/172.3; 435/232.3; 435/252.33; 435/372.1; 435/240.2; 530/380; 530/381; 514/12; 536/23.2; 935/10; 935/14; 935/29; 935/70; 935/73
[58] Field of Search ................................ 435/172.3, 320.1, 435/240.2, 69.6, 212, 226, 252.3; 514/12; 530/380, 381; 536/23.2

[56] References Cited

U.S. PATENT DOCUMENTS

| | | | |
|---|---|---|---|
| 4,652,639 | 3/1987 | Stabinsky | 536/23.1 |
| 4,775,624 | 10/1988 | Bang et al. | 435/226 |
| 4,935,349 | 6/1990 | McKnight | 435/695 |
| 4,959,318 | 9/1990 | Foster et al. | 435/69.1 |
| 4,968,626 | 11/1990 | Foster et al. | 435/320 |
| 4,992,373 | 2/1991 | Bang et al. | 435/226 |
| 5,135,854 | 8/1992 | MacKay et al. | 435/69.1 |
| 5,151,268 | 9/1992 | Bang et al. | 424/94.64 |
| 5,270,178 | 12/1993 | Gerlitz et al. | 435/69.6 |

FOREIGN PATENT DOCUMENTS

| | | | |
|---|---|---|---|
| 38906/89 | 2/1990 | Australia . | |
| 0215548 | 3/1987 | European Pat. Off. | C12N 15/00 |
| 0319312 | 6/1989 | European Pat. Off. | C12N 15/00 |
| 0323149 | 7/1989 | European Pat. Off. | C12N 15/00 |
| WO8704722 | 8/1987 | WIPO | C12N 15/00 |

OTHER PUBLICATIONS

Fort Kamp, E., et al., 1986, DNA, 5(6):511–517.
Berg et al. (1989) Mol. Cell. Biol. 9(11), 5248–5253.
Grinnet et al. (1987) Bio/Technology 5, 1189–1192.
Madden et al. (1990) Thromb. Res. 53, 425–35 (Abstract only).
Toole et al. (1986) Proc. Natl. Acad. Sci. 83, 5939–5942.
Hau, L., and Salem, H., 1988, Thrombosis and Haemostasis 60:267–270.
Walls et al., Abstract and Slides from a presentation on "Role of Glycosylation in the Processing and Function of Recombinant Human Protein C" given at the UCLA Symposium in Keystone, Colorado in Apr., 1990.

*Primary Examiner*—Robert A. Wax
*Assistant Examiner*—William W. Moore
*Attorney, Agent, or Firm*—Douglas K. Norman; John C. Demeter; Gerald V. Dahling

[57] ABSTRACT

A method for the recombinant production of forms of human protein C with higher activity is described. These forms differ from native protein C in their increased amidolytic and functional activities and novel carbohydrate structures. DNA compounds, vectors, and transformants useful in the method are also disclosed.

14 Claims, 7 Drawing Sheets

Restriction Site and Function Map of Plasmid pLPC-Q313 pLPC-Q313

Restriction Site and Function Map of Plasmid pLPC-Q097 pLPC-Q097

Restriction Site and Function Map of Plasmid pLPC-Q248 pLPC-Q248

Restriction Site and Function Map of Plasmid pLPC-Q313 pLPC-Q313

Restriction Site and Function Map of Plasmid pLPC-Q329 pLPC-Q329

Restriction Site and Function Map of Plasmid pGTC pGTC

Restriction Site and Function Map of Plasmid pGT-d pGT-d

Restriction Site and Function Map of Plasmid pGT-h pGT-h

VECTORS AND COMPOUNDS FOR EXPRESSION OF GLYCOSYLATION MUTANTS OF HUMAN PROTEIN C

CROSS-REFERENCE

This application is a continuation of application Ser. No. 07/628,063, filed on Dec. 21, 1990, now abandoned, which is a continuation-in-part of application Ser. No. 07/484,081, filed on Feb. 23, 1990, now abandoned.

SUMMARY OF THE INVENTION

The present invention provides novel DNA compounds and recombinant DNA cloning vectors that encode novel zymogen forms of human protein C. These zymogens have been engineered such that the glycosylation patterns are drastically altered in comparison to the wild type human protein C zymogen. Glycosylation, particularly when the carbohydrate moities contain high levels of sialic acid, may play an important role in protein secretion and function. The novel zymogens of the present invention have been constructed so that each of the glycosylation sites have been individually altered. The expression vectors provide a simple and efficient means for expressing these human protein C zymogens in recombinant host cells. The present invention provides methods for producing zymogen forms of protein C which upon activation have higher amidolytic and anticoagulant activity than the native form. The novel zymogen forms of human protein C differ from those known in the art in the amino acid residue sequence of the various glycosylation sites. These novel zymogen forms of protein C offer special advantages in the treatment of blood disorders involving coagulation.

BACKGROUND OF THE INVENTION

The Role of Protein C in the Regulation of Blood Coagulation

Protein C, a vitamin K dependent plasma protein, is of major physiological importance in the control of hemostasis. Protein C is synthesized as an inactive molecule, herein called nascent protein C. Nascent protein C undergoes complex processing, giving rise to a number of different inactive molecules as is more fully described below. Inactive, secreted forms of protein C are referred to herein as zymogen protein C. Activation of protein C occurs in the blood by a reaction involving a thrombomodulin-thrombin complex. Activated protein C, together with its cofactor protein S, is an anticoagulant of important physiological significance. Activated protein C can prevent intravascular thrombosis and control the extension of existing clots. The mechanism of action of the activated form of protein C and the mechanism of activation of the inactive zymogen into the active protease have been clarified in recent years (for review, see J. E. Gardiner and J. H. Griffin, *Progress in Hematology*, Vol. XIII, pp. 265–278, ed. Elmer B. Brown, Grune and Stratton, Inc., 1983) and Esmon, N. L. 1989, *Prog. Hemost. Thromb.* 9:29–55).

The activation of protein C involves thrombin, the final serine protease in the coagulation cascade, and an endothelial cell membrane-associated glycoprotein called thrombomodulin. Thrombomodulin forms a tight, stoichiometric complex with thrombin. Thrombomodulin, when complexed with thrombin, dramatically changes the functional properties of thrombin. Thrombin normally clots fibrinogen, activates platelets, and converts clotting cofactors V and VIII to their activated forms, Va and VIIIa. Finally, thrombin activates protein C, but only very slowly and inefficiently, and the activation is further inhibited by physiological $Ca^{2+}$. In contrast, thrombin complexed with thrombomodulin does not clot fibrinogen, activate platelets, or convert clotting factors V and VIII to their activated counterparts Va and VIIIa, but does become a very efficient activator of protein C zymogen in the presence of physiological $Ca^{2+}$. The rate constant of protein C zymogen activation by thrombomodulin-thrombin is over 1,000 fold higher than the rate constant for thrombin alone.

To understand how activated protein C down-regulates blood coagulation, the following brief description of the coagulation enzyme system is provided. The coagulation system is best looked at as a chain reaction involving the sequential activation of zymogens into active serine proteases. This chain reaction eventually produces the enzyme thrombin, which through limited proteolysis converts plasma fibrinogen into the insoluble gel fibrin. Two key events in the coagulation cascade are the conversion of clotting factor X to Xa by clotting factor IXa and the conversion of prothrombin into thrombin by clotting factor Xa. Both of these reactions occur on cell surfaces, most notably the platelet surface, and both reactions require cofactors. The major cofactors, factors V and VIII, in the system circulate as relatively inactive precursors, but when the first few molecules of thrombin are formed, thrombin loops back and activates the cofactors through limited proteolysis. The activated cofactors, Va and VIIIa, accelerate both the conversion of prothrombin into thrombin and also the conversion of factor X to factor Xa by approximately five orders of magnitude. Activated protein C preferentially acts on, to proteolytically degrade, hydrolyze, and irreversibly destroy clotting cofactors Va and VIIIa, the activated forms of the inactive clotting factors V and VIII. Clotting factors V and VIII, in contrast, are very poor substrates for activated protein C in vivo.

An important cofactor for activated protein C is protein S, another vitamin K-dependent plasma protein. Protein S substantially increases activated protein C-mediated hydrolysis of factors Va and VIIIa 25 fold.

Protein C as a Therapeutic Agent

Protein C is recognized as a valuable therapeutic agent (see, for example, Bang et al., U.S. Pat. No. 4,775,624, issued Oct. 4, 1988, the teaching of which is incorporated herein by reference). Activated protein C is a novel antithrombotic agent with a wider therapeutic index than available anticoagulants, such as heparin and the oral hydroxycoumarin type anticoagulants. Neither zymogen protein C nor activated protein C is effective until thrombin is generated, because thrombin is needed to convert clotting factors V to Va and VIII to VIIIa; the activated forms of these two cofactors are the preferred substrate for activated protein C. Thrombin is also required to activate zymogen protein C, for without the thrombomodulin-thrombin complex, the protein C zymogen is not efficiently converted into its active counterpart.

Activated protein C is an on-demand anti-coagulant, because activated protein C works by inactivating cofactors Va and VIIIa. Because thrombin is required to convert factors V and VIII to their activated counterparts Va and VIIIa, protein C only acts as an anticoagulant after thrombin is generated. Conventional anticoagulants, in contrast to activated protein C, maintain a constant anticoagulant state throughout the circulation for as long as they are given to the patient, thereby substantially increasing the risk of bleeding complications over that for protein C or activated protein C.

Activated protein C is therefore an on-demand anticoagulant of wide clinical utility for use as an alternative to heparin and the hydroxycoumarins.

In some disease states, such as hereditary protein C deficiency, protein C zymogen is of great therapeutic importance. In congenital homozygous protein C deficiency, affected individuals die in early childhood from purpura fulminans, an often lethal form of disseminated intravascular coagulation. In heterozygous protein C deficiency, affected individuals suffer severe, recurrent thromboembolic episodes. It is well established clinically that plasma protein concentrates designed to treat hemophilia B or factor IX deficiency, which contain protein C as an impurity, are effective in the prevention and treatment of intravascular clotting in heterozygous protein C deficiency. Protein C levels have also been noted to be abnormally low in thrombotic states such as disseminated intravascular coagulation and in disease states predisposing to thrombosis, such as major trauma, major surgery, and cancer.

The Synthesis and Activation of Human Protein C

To facilitate an understanding of the activation of protein C and the invention, the coding sequence, and corresponding amino acid residue sequence, for nascent human protein C is depicted below. This amino acid residue sequence, and relevant portions thereof, also characterizes "native human protein C" for purposes of the present invention.

wherein A is deoxyadenyl, G is deoxyguanyl, C is deoxycytidyl, T is thymidyl, ALA is Alanine, ARG is Arginine, ASN is Asparagine, ASP is Aspartic acid, —COOH is the carboxy terminus, CYS is Cysteine, GLN is Glutamine, GLU is Glutamic Acid, GLY is Glycine, HIS is Histidine, $H_2N$- is the amino terminus, ILE is Isoleucine, LEU is Leucine, LYS is Lysine, MET is Methionine, PHE is Phenylalanine, PRO is Proline, SER is Serine, THR is Threonine, TRP is Tryptophan, TYR is Tyrosine, and VAL is Valine.

The DNA sequence depicted above was derived from cDNA clones prepared from human liver mRNA that encodes human protein C. Those skilled in the art recognize that the degenerate nature of the genetic code enables one to construct many different DNA sequences that encode the same amino acid residue sequence. The cDNA sequence for nascent human protein C depicted above is thus only one of many possible nascent human protein C-encoding sequences. In constructing the cDNA clones, a 5' poly G sequence, a 3' poly C sequence, and both 5' and 3' PstI restriction enzyme recognition sequences were constructed at the ends of the protein C-encoding cDNA. Two of these cDNA clones were manipulated to construct a DNA molecule comprising both the coding sequence of nascent human protein C and also portions of the DNA encoding the untranslated mRNA at the 5' and 3' ends of the coding region. This DNA molecule was inserted into the PstI site of plasmid pBR322 to construct plasmid pHC7. Plasmid pHC7 thus comprises the coding sequence above and, again depicting only one strand of the molecule, also contains these additional sequences:

5'-C TGCAGG GGG GGG GGG GGG GGG GGG CTG TCATGG CGG CAG GAC GGCGAACTTGCAGTATCTCCACGACCCGCCCCTACAGGTGCC AGTGCCTCCAGA-3' and

5'-CGACCCTCCCTG CAG GGCTGG GCTTTTGCATGG CAATGG ATG GGA CATTAAAGG GACATG TAACAAGCACACCCCCCCCCCCCCCCCC CCCCCCCCTGCAG-3' at the 5' and 3' ends, respectively, of the coding strand of the nascent human protein C coding sequence. Due to the complementary nature of DNA base-pairing, the sequence of one strand of a double-stranded DNA molecule is sufficient to determine the sequence of the opposing strand. Plasmid pHC7 can be conventionally isolated from *E. coli* K12 RR1/pHC7, a strain deposited with and made part of the permanent stock culture collection of the Northern Regional Research Laboratory (NRRL), Peoria, Ill. A culture of *E. coli* K12 RR1/pHC7 can be obtained from the NRRL under the accession number NRRL B-15926. A restriction site and function map of plasmid pHC7 is presented in FIG. 2 of the accompanying drawings.

Nascent protein C can also be depicted schematically, as shown below.

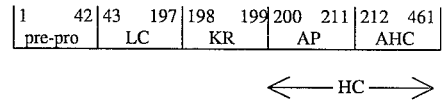

pre-pro—amino acid residues 1–42 of nascent human protein C encode the signal peptide and pro—peptide of human protein C, important for directing secretion and γ-carboxylation of protein C.

LC—amino acid residues 43–197 of nascent protein C, once post—translationally modified, constitute the light chain (LC) of both the two-chain zymogen (formed from one-chain zymogen by removal of the KR dipeptide, as discussed below) and activated forms of protein C.

KR—amino acid residues 198–199 of nascent human protein C; these residues are believed to be removed (on the basis of homology with bovine protein C), probably by a two-step process comprising a first cleavage (either between residues 197–198 or 199–200) followed by carboxypeptidase or aminopeptidase action, to form two-chain protein C.

AP—amino acid residues 200–211 of nascent protein C constitute the activation peptide, which is removed from the zymogen forms of protein C to obtain activated protein C.

AHC—amino acid residues 212–461 of nascent protein C, once post-translationally modified, constitute the activated heavy chain (AHC) of active protein C.

HC—the heavy chain of the two chain form of protein C zymogen, once post-translationally modified, is composed of amino acid residues 200–461, the AP and AHC.

Human protein C zymogen is a serine protease precursor synthesized in the liver and present in the blood. For expression of complete biological activity, protein C requires post—translational modifications for which vitamin K is needed. The two-chain, disulfide-linked, protein C zymogen arises from the single-chain zymogen by limited proteolysis. This limited proteolysis is believed to include cleavage and removal of amino acid residues 198 and 199. The activation of the two-chain zymogen into the active serine protease involves the proteolytic cleavage of an ARG-LEU peptide bond (residues 211 and 212). This latter cleavage releases a dodecapeptide (residues 200–211), the activation peptide, that constitutes the amino-terminus of the larger (heavy) chain of the two-chain zymogen molecule. Protein C is significantly glycosylated; the mature enzyme from plasma reportedly contains 15 to 23% carbohydrate. Protein C also contains a number of unusual amino acids, including γ-carboxyglutamic acid and β-hydroxyaspartic acid (erythro-L-β-hydroxy aspartate). γ-carboxyglutamic acid (gla) is produced by γ-glutamyl carboxylation from glutamic acid residues with the aid of a hepatic microsomal carboxylase which requires vitamin K as a cofactor.

The activation of human protein C can also be represented schematically and is shown below. Those skilled in the art recognize that the order of the steps shown in the schematic do not necessarily reflect the order of the steps in the in vivo pathway.

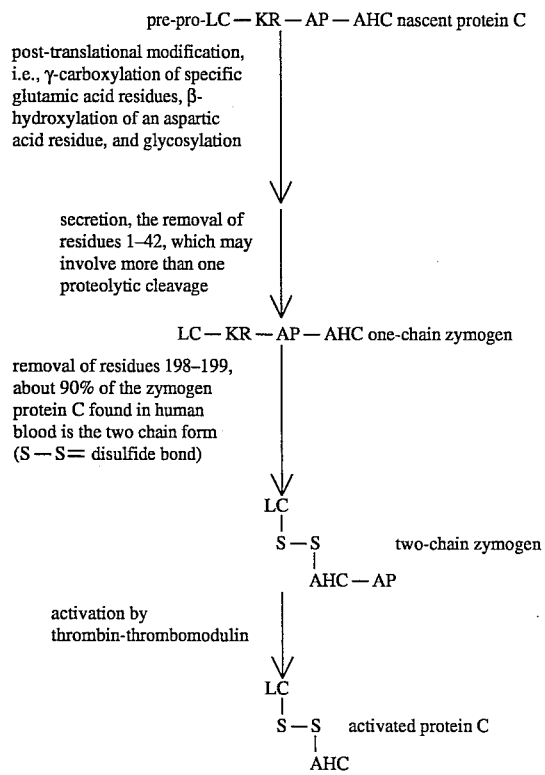

The present invention provides novel compounds, vectors, transformants, and methods for the recombinant expression of novel protein C zymogens.

Definitions

For purposes of the present invention, as disclosed and claimed herein, the following terms are as defined below.

Ad2LP—the major late promoter of adenovirus type 2.

Amino acid residues in proteins or peptides described herein as abbreviated as follows in Table I.

TABLE I

| Three-Letter Abbreviation | Amino Acid Residue | One-Letter Abbreviation |
|---|---|---|
| PHE | Phenylalanine | F |
| LEU | Leucine | L |
| ILE | Isoleucine | I |
| MET | Methionine | M |
| VAL | Valine | V |
| SER | serine | S |
| PRO | Proline | P |
| THR | Threonine | T |
| ALA | Alanine | A |
| TYR | Tyrosine | Y |
| HIS | Histidine | H |
| GLN | Glutamine | Q |
| ASN | Asparagine | N |
| LYS | Lysine | K |
| ASP | Aspartic Acid | D |
| GLU | Glutamic Acid | E |
| CYS | Cysteine | C |
| TRP | Tryptophan | W |
| ARG | Arginine | R |
| GLY | Glycine | G |

ApR—the ampicillin—resistant phenotype or gene conferring same.

BK—DNA from BK virus.

Enh or enhancer—the enhancer of BK virus.

ep or SV40ep—a DNA segment comprising the SV40 early promoter of the T-antigen gene, the T-antigen binding sites, the SV40 enhancer, and the SV40 origin of replication.

γ-carboxylation—a reaction which adds a carboxyl group to glutamic acids at the γ-carbon.

γ-carboxylated protein—a protein in which some glutamic acids residues have undergone γ-carboxylation.

GBMT transcription unit—a modified transcription control unit comprising the P2 enhancer of BK virus spaced closely to the upstream regulatory element of the adenovirus major late promoter (MLTF), the adenovirus-2 major late promoter, a poly GT element positioned to stimulate said promoter and a DNA sequence containing the spliced tripartite leader sequence of adenovirus. The GBMT transcription unit is found on an approximately 900 base pair HindIII restriction fragment of plasmid pGT-h.

IVS—DNA encoding an intron, also called an intervening sequence.

MMTpro—the promoter of the mouse metallothionein-I gene.

Nascent protein—the polypeptide produced upon translation of a mRNA transcript, prior to any post-translational modifications. However, post-translational modifications such as γ-carboxylation of glutamic acid residues and hydroxylation of aspartic acid residues may begin to occur before a protein is fully translated from an mRNA transcript.

NeoR—a neomycin resistance-conferring gene, which can also be used to confer resistance to the antibiotic G418.

pA—a DNA sequence encoding a polyadenylation signal.

Promoter—a DNA sequence that directs transcription of DNA into RNA.

Protein C activity—any property of human protein C responsible for proteolytic, amidolytic, esterolytic, and biological (anticoagulant or profibrinolytic) activities. Methods for testing for protein anticoagulant activity are well known in the art, i.e., see Grinnell et al., 1987, Biotechnology 5:1189.

Recombinant DNA Cloning Vector—any agent, including, but not limited to; chromosomally integrating agents, autonomously replicating plasmids, and phages, comprising a DNA molecule to which One or more additional DNA segments can be or have been added.

Recombinant DNA Expression Vector—any recombinant DNA cloning vector into which a promoter has been incorporated and positioned to drive expression of a gene product.

Recombinant DNA Vector—any recombinant DNA cloning or expression vector.

Replicon—A DNA sequence that controls and allows for autonomous replication of a plasmid or other vector.

Restriction Fragment—any linear DNA sequence generated by the action of one or more restriction endonuclease enzymes.

Sensitive Host Cell—a host cell that cannot grow in the presence of a given antibiotic or other toxic compound without a DNA segment that confers resistance thereto.

TcR—the tetracycline—resistant phenotype or gene conferring same.

Transformation—the introduction of DNA into a recipient host cell that changes the genotype of the recipient cell.

Transformant—a recipient host cell that has undergone transformation.

Translational Activating Sequence—any DNA sequence, inclusive of that encoding a ribosome binding site and translational start codon, such as 5'-ATG-3', that provides for the translation of a mRNA transcript into a peptide or polypeptide.

Zymogen—an enzymatically inactive precursor of a proteolytic enzyme. Protein C zymogen, as used herein, refers to secreted, inactive forms, whether one chain or two chain, of protein C.

DETAILED DESCRIPTION OF THE INVENTION

Figure 1:
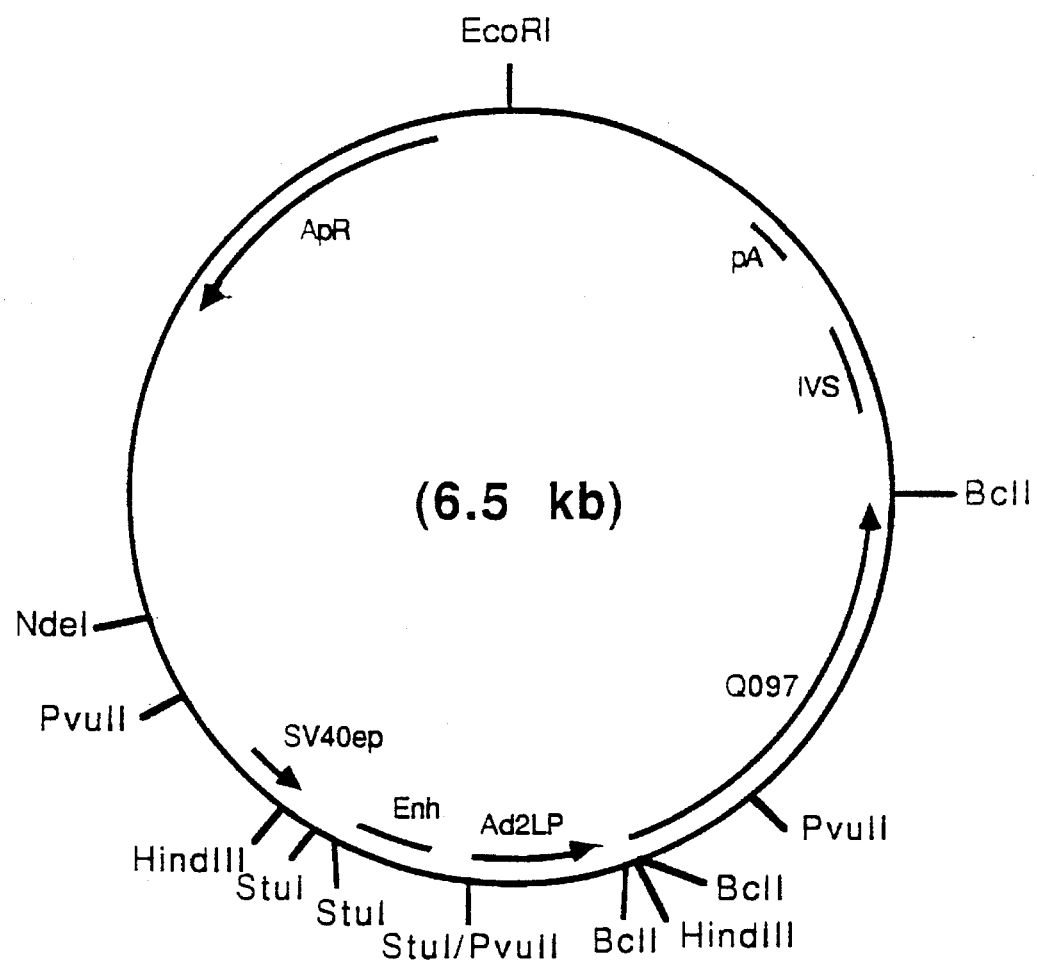
FIG. 1 is a restriction site and function map of plasmid pLPC-Q097. For purposes of the present disclosures, the Figures are not drawn exactly to scale.
Figure 2:
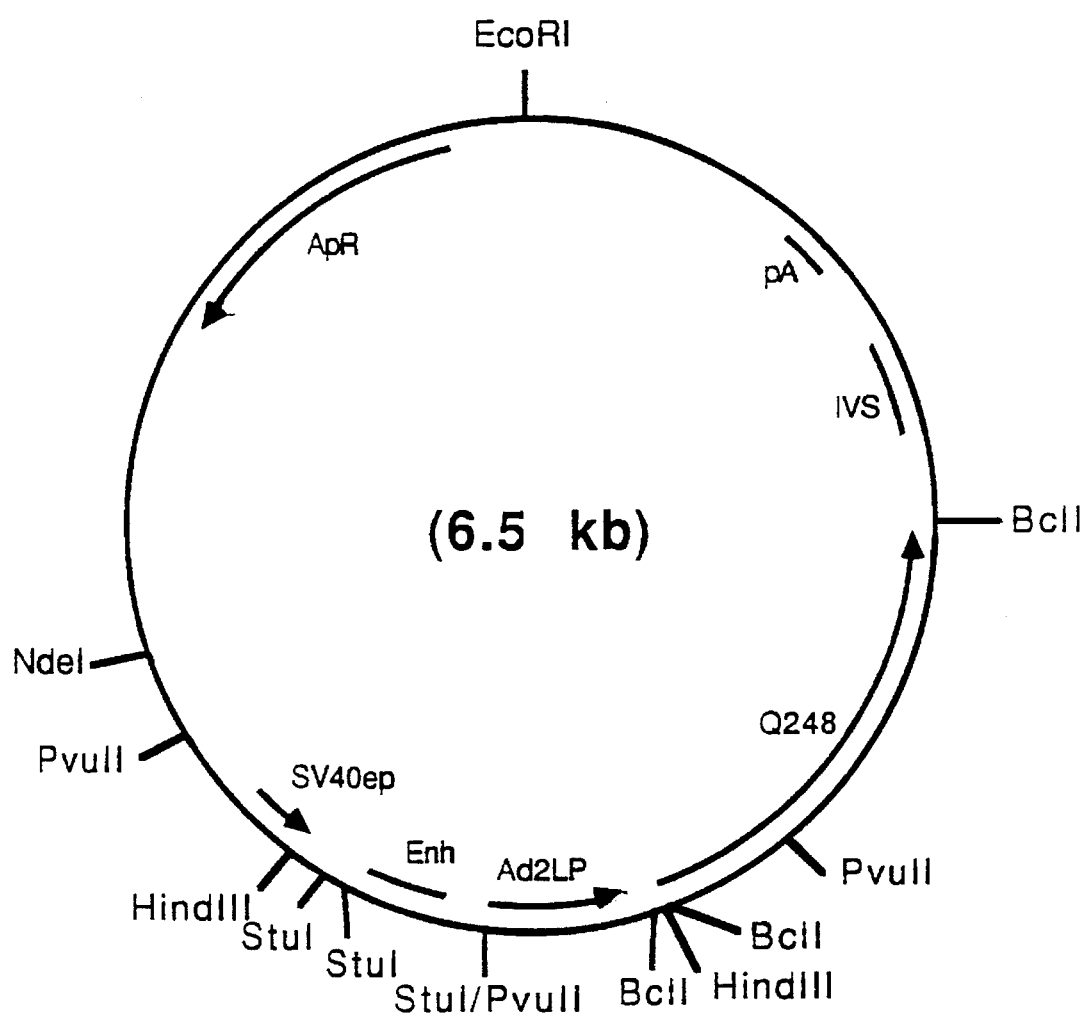
FIG. 2 is a restriction site and function map of plasmid pLPC-Q248.
Figure 3:
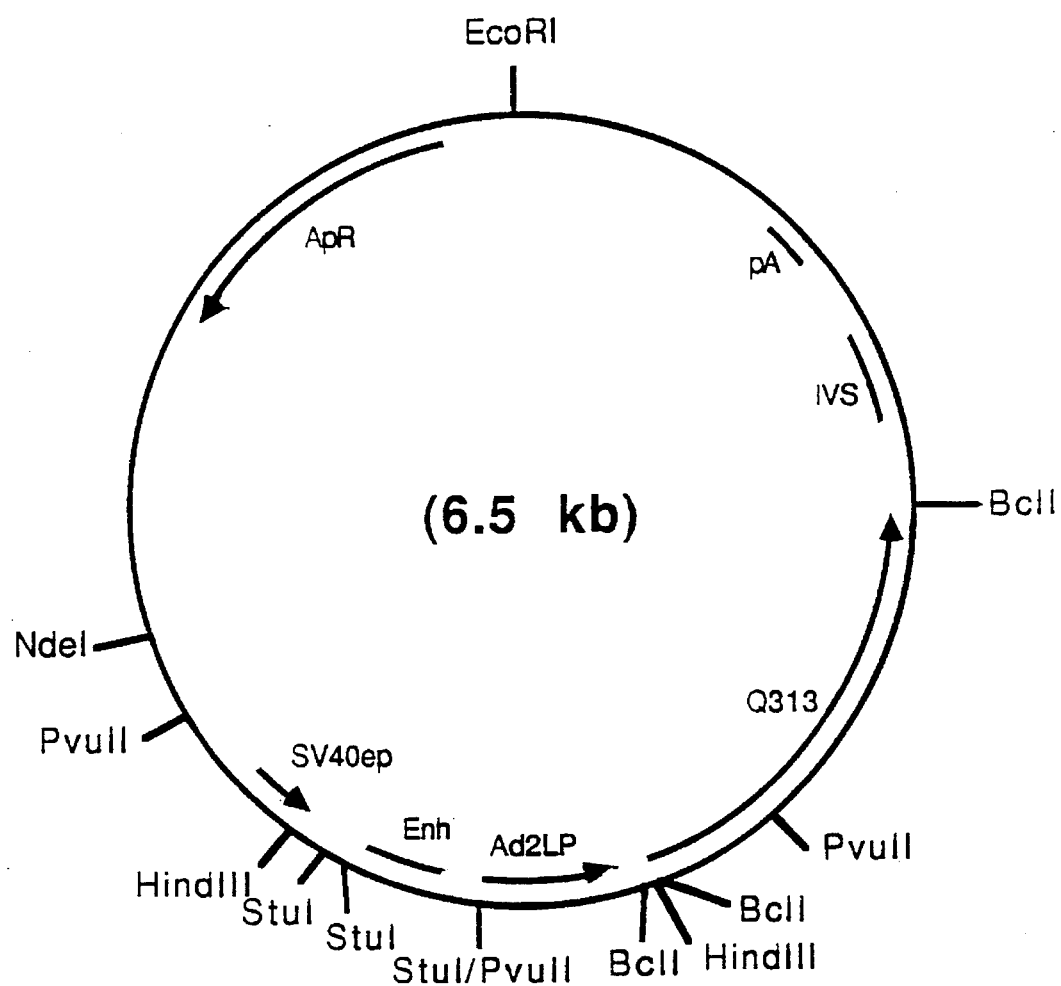
FIG. 3 is a restriction site and function map of plasmid pLPC-Q313.
Figure 4:
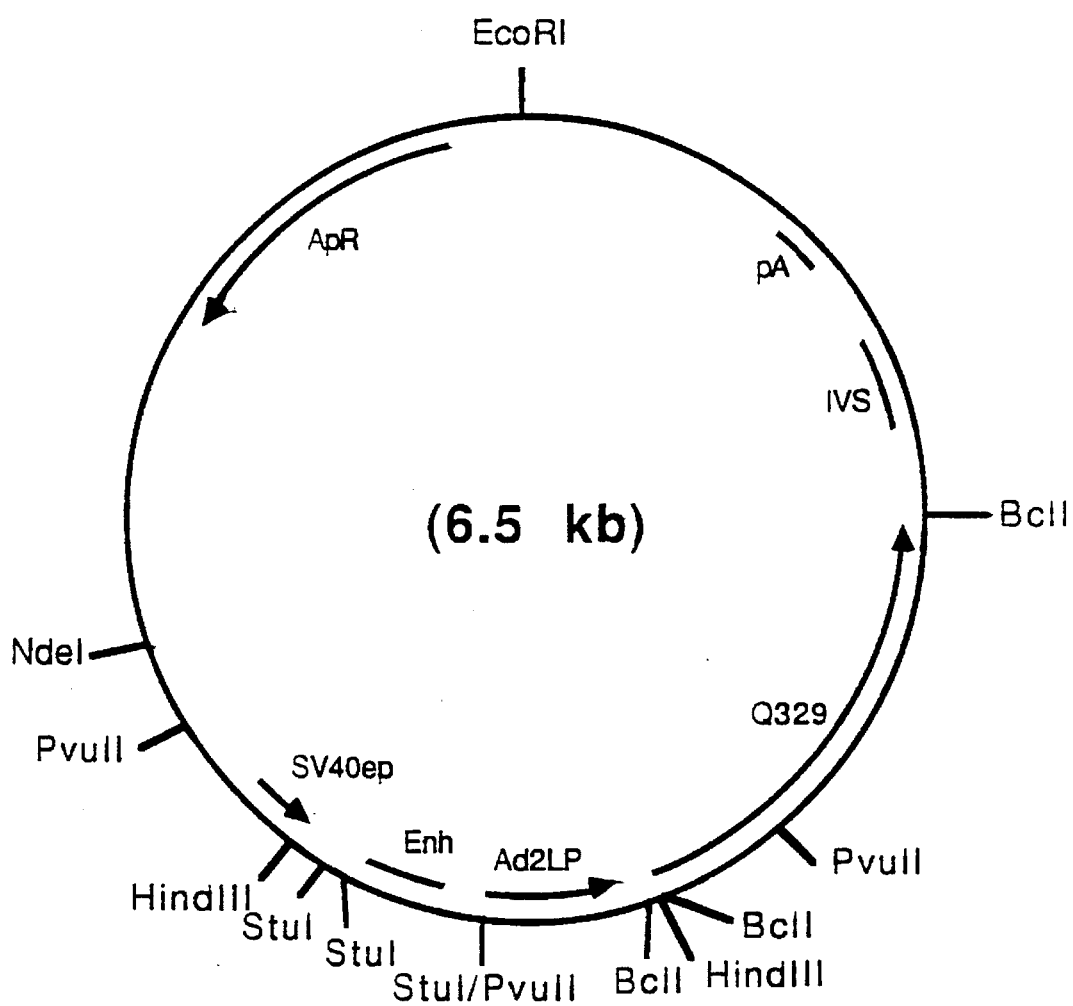
FIG. 4 is a restriction site and function map of plasmid pLPC-Q329.
Figure 5:
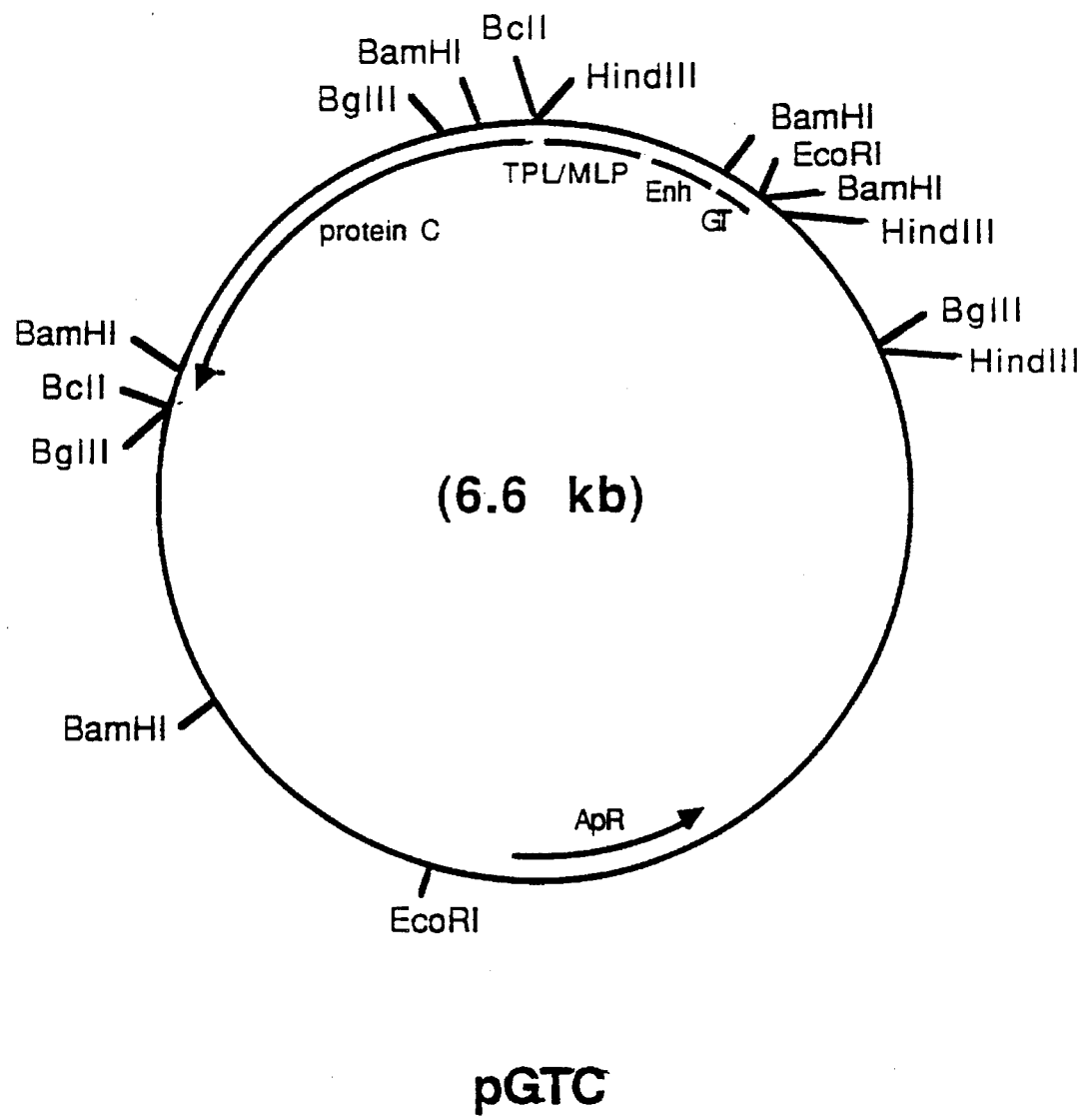
FIG. 5 is a restriction site and function map of plasmid pGTC.
Figure 6:
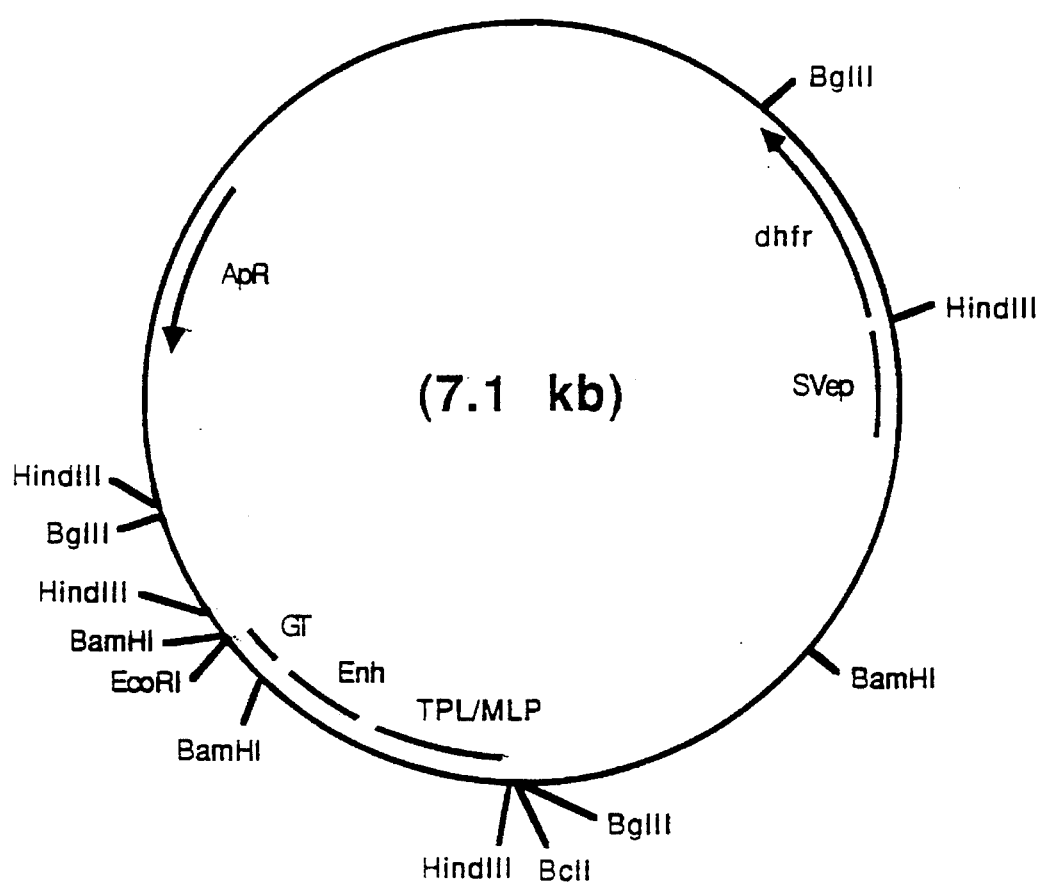
FIG. 6 is a restriction site and function map of plasmid pGT-d.
Figure 7:
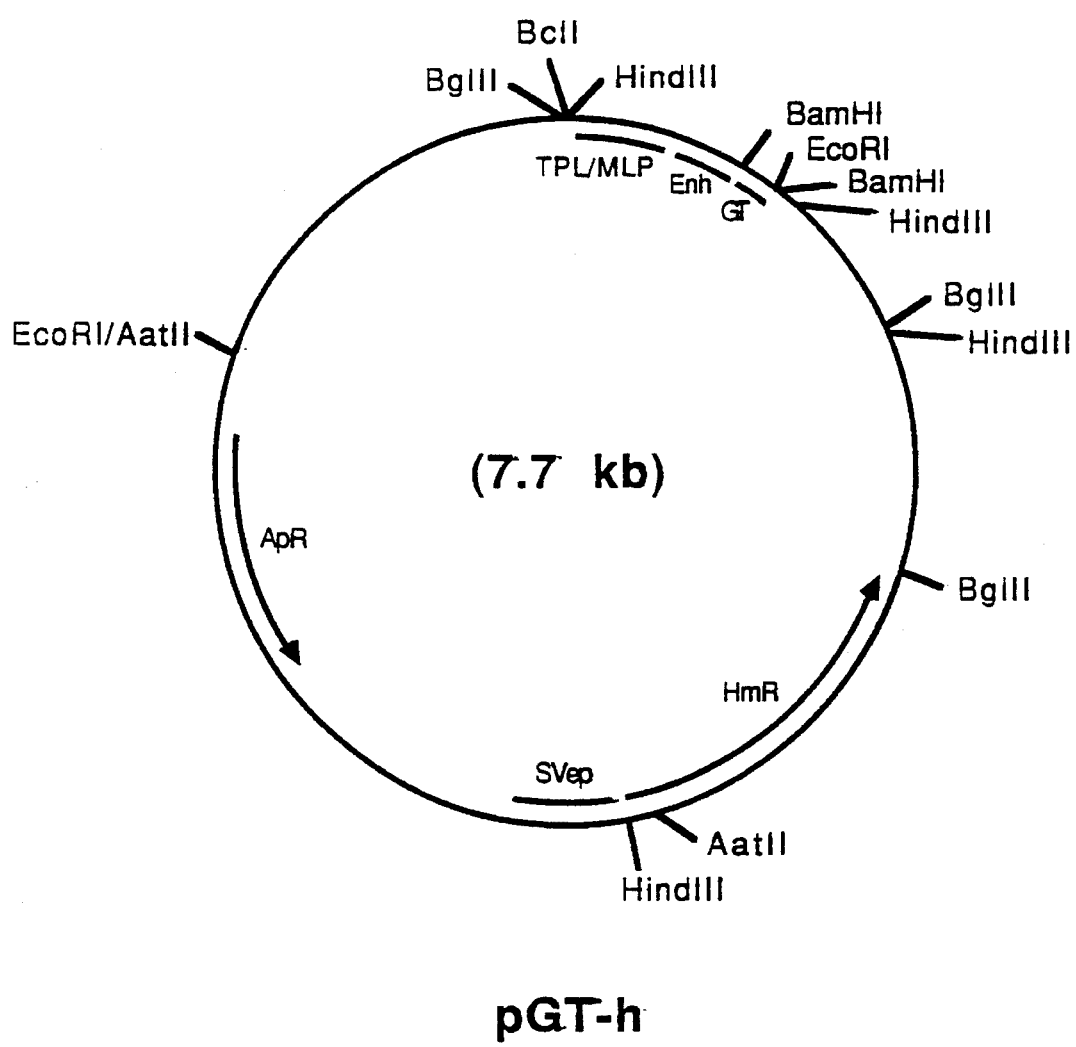
FIG. 7 is a restriction site and function map of plasmid pGT-h.

The present invention provides DNA compounds that code for the expression of novel zymogen forms of human protein C. Several methods of producing native human protein C zymogen and native human protein C have been described (see Bang et al., U.S. Pat. No. 4,775,624, issued Oct. 4, 1988 and European Patent Publication 215548, both of which are herein incorporated by reference). These prior art methods provide for the expression of zymogen forms of human protein C that do not differ in amino acid sequence from the zymogen forms present in human blood. When expressed in certain eukaryotic cell lines, such as the human kidney 293 cell line, the native human protein C zymogen is secreted with a novel glycosylation pattern which is unlike the zymogen form found in human blood (see Grinnell, U.S. patent application Ser. No. 07/368,700, Attorney Docket No. X-6606C, filed Jun. 20, 1989, entire teaching of which is herein incorporated by reference).

The present invention provides zymogen forms of human protein C which have altered glycosylation patterns due to site-directed changes in the amino acid residue sequence. When activated these zymogen forms have an increased amidolytic and anticoagulant activity when compared to native human protein C. The present invention also provides DNA compounds, recombinant DNA expression vectors, transformed cell lines, and methods for the recombinant expression of these novel zymogen forms of human protein C. The method for producing these zymogen forms of human protein C comprises:

(A) transforming a eukaryotic host cell with a recombinant DNA vector, said vector comprising,
   (i) a DNA sequence that encodes an amino acid residue sequence, said amino acid residue sequence comprising, from the amino terminus to the carboxy terminus, the amino acid sequence:

| MET | TRP | GLN | LEU | THR | SER | LEU | LEULEU | PHE | VAL | ALA | THR | TRP | GLY | ILE |
|-----|-----|-----|-----|-----|-----|-----|--------|-----|-----|-----|-----|-----|-----|-----|
| SER | GLY | THR | PRO | ALA | PRO | LEU | ASPSER | VAL | PHE | SER | SER | SER | GLU | ARG |
| ALA | HIS | GLN | VAL | LEU | ARG | ILE | ARG LYS | ARG | ALA | ASN | SER | PHE | LEU | GLU |
| GLU | LEU | ARG | HIS | SER | SER | LEU | GLUARG | GLU | CYS | ILE | GLU | GLU | ILE | CYS |
| ASP | PHE | GLU | GLU | ALA | LYS | GLU | ILEPHE | GLN | ASN | VAL | ASP | ASP | THR | LEU |
| ALA | PHE | TRP | SER | LYS | HIS | VAL | ASPGLY | ASP | GLN | CYS | LEU | VAL | LEU | PRO |
| LEU | GLU | HIS | PRO | CYS | ALA | SER | LEUCYS | CYS | GLY | HIS | GLY | THR | CYS | ILE |
| ASP | GLY | ILE | GLY | SER | PHE | SER | CYSASP | CYS | ARG | SER | GLY | TRP | GLU | GLY |
| ARG | PHE | CYS | GLN | ARG | GLU | VAL | SERPHE | LEU | R¹ | CYS | SER | LEU | ASP | ASN |
| GLY | GLY | CYS | THR | HIS | TYR | CYS | LEUGLU | GLU | VAL | GLY | TRP | ARG | ARG | CYS |

-continued

| | | | | | | | | | | | | | | |
|---|---|---|---|---|---|---|---|---|---|---|---|---|---|---|
| SER | CYS | ALA | PRO | GLY | TYR | LYS | LEUGLY | ASP | ASP | LEU | LEU | GLN | CYS | HIS |
| PRO | ALA | VAL | LYS | PHE | PRO | CYS | GLYARG | PRO | TRP | LYS | ARG | MET | GLU | LYS |
| LYS | ARG | SER | HIS | LEU | LYS | ARG | ASPTHR | GLU | ASP | GLN | GLU | ASP | GLN | VAL |
| ASP | PRO | ARG | LEU | ILE | ASP | GLY | LYSMET | THR | ARG | ARG | GLY | ASP | SER | PRO |
| TRP | GLN | VAL | VAL | LEU | LEU | ASP | SERLYS | LYS | LYS | LEU | ALA | CYS | GLY | ALA |
| VAL | LEU | ILE | HIS | PRO | SER | TRP | VALLEU | THR | ALA | ALA | HIS | CYS | MET | ASP |
| GLU | SER | LYS | LYS | LEU | LEU | VAL | ARG LEU | GLY | GLU | TYR | ASP | LEU | ARG | ARG |
| TRP | GLU | LYS | TRP | GLU | LEU | ASP | LEUASP | ILE | LYS | GLU | VAL | PHE | VAL | HIS |
| PRO | R₂ | TYR | SER | LYS | SER | THR | THRASP | ASN | ASP | ILE | ALA | LEU | LEU | HIS |
| LEU | ALA | GLN | PRO | ALA | THR | LEU | SERGLN | THR | ILE | VAL | PRO | ILE | CYS | LEU |
| PRO | ASP | SER | GLY | LEU | ALA | GLU | ARG GLU | LEU | ASN | GLN | ALA | GLY | GLN | GLU |
| THR | LEU | VAL | THR | GLY | TRP | GLY | TYRHIS | SER | SER | ARG | GLU | LYS | GLU | ALA |
| LYS | ARG | R₃ | ARG | THR | PHE | VAL | LEUASN | PHE | ILE | LYS | ILE | PRO | VAL | VAL |
| PRO | HIS | R₄ | GLU | CYS | SER | GLU | VALMET | SER | ASN | MET | VAL | SER | GLU | ASN |
| MET | LEU | CYS | ALA | GLY | ILE | LEU | GLYASP | ARG | GLN | ASP | ALA | CYS | GLU | GLY |
| ASP | SER | GLY | GLY | PRO | MET | VAL | ALASER | PHE | HIS | GLY | THR | TRP | PHE | LEU |
| VAL | GLY | LEU | VAL | SER | TRP | GLY | GLUGLY | CYS | GLY | LEU | LEU | HIS | ASN | TYR |
| GLY | VAL | TYR | THR | LYS | VAL | SER | ARG TYR | LEU | ASP | TRP | ILE | HIS | GLY | HIS |
| ILE | ARG | ASP | LYS | GLU | ALA | PRO | GLNLYS | SER | TRP | ALA | PRO—COOH | | | | wherein R₁ is selected from the group consisting of ASN and GLN, R₂ is selected from the group consisting of ASN and GLN, R₃ is selected from the group consisting of ASN and GLN and R₄ is selected from the group consisting of ASN and GLN; and (ii) a promoter positioned to drive expression of said DNA sequence;

(B) culturing said host cell transformed in step (A) under conditions suitable for expression of said DNA sequence; and (C) recovering said protein C zymogen from said culture.

This method and compounds useful in the method are more fully described below.

The invention also provides DNA compounds for use in the method of producing these novel zymogen forms of human protein C. These novel compounds all encode a pre-propeptide comprising a signal peptide for directing secretion and a propeptide from a γ-carboxylated (through the action of a vitamin K-dependent carboxylase) protein. Such propeptide sequences are well-known in the art. See, for example, Suttie et al., 1987, Proc. Natl. Acad. Sci. 84:634–637. Preferably, and for ease of construction, both the signal peptide-coding sequence and the propeptide-coding sequence will be derived from the amino acid residue sequence of the pre-propeptide of a γ-carboxylated protein. Examples of such γ-carboxylated proteins include, but are not limited to, factor VII, factor IX, factor X, prothrombin, protein S, protein Z, and, protein C. A DNA sequence encoding the pre-propeptide of human protein C is most preferred for use in the vectors of the invention.

The DNA compounds of the invention further comprise the coding sequence for the light chain of human protein C positioned immediately adjacent to, downstream of, and in translational reading frame with the pre-propeptide coding sequence. The light chain of human protein C contains amino acid residues 43 to 197, inclusive, of nascent protein C, as depicted in the background section above. The amino-terminal portions of the vitamin K-dependent plasma proteins, such as the amino-terminal portion of the light chain of protein C, have calcium-binding sites. The calcium-binding domains of these plasma proteins, such as factor VII, factor IX, factor X, prothrombin, and protein S, may be used in a manner (see European Patent Publication No. 0215548A1, at pages 12 and 13) equivalent to the calcium-binding domain of the light chain of human protein C. In one of the novel zymogen forms (Q097) of the present invention, the asparagine residue at position 139 within the light chain has been changed into a glutamine residue, thereby removing the glycosylation site.

The DNA compounds of the invention further comprise the coding sequence for the dipeptide LYS-ARG (KR) positioned immediately adjacent to, downstream of, and in translational reading frame with the light chain coding sequence. A dibasic dipeptide such as LYS-ARG is positioned in the nascent protein at the carboxyl-terminal side of the light chain. The orientation of the LYS-ARG dipeptide in the expressed protein is irrelevant for purposes of the present invention. Dibasic dipeptides such as LYS-LYS or ARG-ARG are equivalent to the LYS-ARG dipeptide for purposes of the present invention. For purposes of the present invention, however, the dipeptide LYS-ARG, which is the dipeptide in native human protein C, is preferred.

Immediately downstream of the codons for the LYS-ARG dipeptide is the coding sequence of the activation peptide. Various forms of human protein C which have been mutated in the activation region are disclosed in Grinnell, U.S. patent application Ser. No. 07/484,133, Attorney Docket No. X-7808, filed herewith on even date, the entire teaching of which is herein incorporated by reference. Those skilled in the art will recognize that the zymogen forms of the present invention primarily differ from native zymogen forms of human protein C as described below.

Other amino acid substitutions, in addition to the substitution at position 139 in the light chain, can also enhance the amidolytic and anticoagulant activity of the resulting zymogen. The phrase "resulting zymogen" is used to indicate that although substitutions are described with reference to amino acid positions in nascent human protein C, nascent human protein C must first be secreted (resulting in the removal of amino acid residues 1 through 42) to obtain a zymogen form. Substitution of the asparagine residue at position 139 (in nascent human protein C) for a glutamine residue thus results in a novel zymogen of the present invention. Substitution of the asparagine residue (in the activated heavy chain) at any of positions 290, 355 or 371, for a glutamine residue also results in a novel zymogen form of the present invention.

Thus, the preferred novel zymogen forms of human protein C of the present invention result from processing and secretion of nascent human protein C molecules with the amino acid residue sequence depicted below:

| | | | | | | | | | | | | | | | |
|---|---|---|---|---|---|---|---|---|---|---|---|---|---|---|---|
| MET | TRP | GLN | LEU | THR | SER | LEU | LEULEU | PHE | VAL | ALA | THR | TRP | GLY | ILE |
| SER | GLY | THR | PRO | ALA | PRO | LEU | ASPSER | VAL | PHE | SER | SER | SER | GLU | ARG |
| ALA | HIS | GLN | VAL | LEU | ARG | ILE | ARG LYS | ARG | ALA | ASN | SER | PHE | LEU | GLU |
| GLU | LEU | ARG | HIS | SER | SER | LEU | GLUARG | GLU | CYS | ILE | GLU | GLU | ILE | CYS |
| ASP | PHE | GLU | GLU | ALA | LYS | GLU | ILEPHE | GLN | ASN | VAL | ASP | ASP | THR | LEU |
| ALA | PHE | TRP | SER | LYS | HIS | VAL | ASPGLY | ASP | GLN | CYS | LEU | VAL | LEU | PRO |
| LEU | GLU | HIS | PRO | CYS | ALA | SER | LEUCYS | CYS | GLY | HIS | GLY | THR | CYS | ILE |
| ASP | GLY | ILE | GLY | SER | PHE | SER | CYSASP | CYS | ARG | SER | GLY | TRP | GLU | GLY |
| ARG | PHE | CYS | GLN | ARG | GLU | VAL | SERPHE | LEU | R$_1$ | CYS | SER | LEU | ASP | ASN |
| GLY | GLY | CYS | THR | HIS | TYR | CYS | LEUGLU | GLU | VAL | GLY | TRP | ARG | ARG | CYS |
| SER | CYS | ALA | PRO | GLY | TYR | LYS | LEUGLY | ASP | ASP | LEU | LEU | GLN | CYS | HIS |
| PRO | ALA | VAL | LYS | PHE | PRO | CYS | GLYARG | PRO | TRP | LYS | ARG | MET | GLU | LYS |
| LYS | ARG | SER | HIS | LEU | LYS | ARG | ASPTHR | GLU | ASP | GLN | GLU | ASP | GLN | VAL |
| ASP | PRO | ARG | LEU | ILE | ASP | GLY | LYSMET | THR | ARG | ARG | GLY | ASP | SER | PRO |
| TRP | GLN | VAL | VAL | LEU | LEU | ASP | SERLYS | LYS | LYS | LEU | ALA | CYS | GLY | ALA |
| VAL | LEU | ILE | HIS | PRO | SER | TRP | VALLEU | THR | ALA | ALA | HIS | CYS | MET | ASP |
| GLU | SER | LYS | LYS | LEU | LEU | VAL | ARG LEU | GLY | GLU | TYR | ASP | LEU | ARG | ARG |
| TRP | GLU | LYS | TRP | GLU | LEU | ASP | LEUASP | ILE | LYS | GLU | VAL | PHE | VAL | HIS |
| PRO | R$_2$ | TYR | SER | LYS | SER | THR | THRASP | ASN | ASP | ILE | ALA | LEU | LEU | HIS |
| LEU | ALA | GLN | PRO | ALA | THR | LEU | SERGLN | THR | ILE | VAL | PRO | ILE | CYS | LEU |
| PRO | ASP | SER | GLY | LEU | ALA | GLU | ARG GLU | LEU | ASN | GLN | ALA | GLY | GLN | GLU |
| THR | LEU | VAL | THR | GLY | TRP | GLY | TYRHIS | SER | SER | ARG | GLU | LYS | GLU | ALA |
| LYS | ARG | R$_3$ | ARG | THR | PHE | VAL | LEUASN | PHE | ILE | LYS | ILE | PRO | VAL | VAL |
| PRO | HIS | R$_4$ | GLU | CYS | SER | GLU | VALMET | SER | ASN | MET | VAL | SER | GLU | ASN |
| MET | LEU | CYS | ALA | GLY | ILE | LEU | GLYASP | ARG | GLN | ASP | ALA | CYS | GLU | GLY |
| ASP | SER | GLY | GLY | PRO | MET | VAL | ALASER | PHE | HIS | GLY | THR | TRP | PHE | LEU |
| VAL | GLY | LEU | VAL | SER | TRP | GLY | GLUGLY | CYS | GLY | LEU | LEU | HIS | ASN | TYR |
| GLY | VAL | TYR | THR | LYS | VAL | SER | ARG TYR | LEU | ASP | TRP | ILE | HIS | GLY | HIS |
| ILE | ARG | ASP | LYS | GLU | ALA | PRO | GLNLYS | SER | TRP | ALA | PRO—COOH | | | | wherein R$_1$ is selected from the group consisting of ASN and GLN, R$_2$ is selected from the group consisting of ASN and GLN, R$_3$ is selected from the group consisting of ASN and GLN and R$_4$ is selected from the group consisting of ASN and GLN.

Novel zymogen Q097 comprises a substitution of the asparagine residue at position 139 with a glutamine residue. Zymogen Q248 substitutes the asparagine residue at position 290 with a glutamine residue. Zymogen Q313 substitutes the aspargine residue at position 355 with a glutamine residue while zymogen Q329 substitutes the asparagine residue at position 371 with a glutamine residue.

Those skilled in the art will recognize that, due to the degeneracy of the genetic code, a variety of DNA compounds can encode the polypeptide depicted above. Consequently, the constructions described below and in the accompanying Examples for the preferred DNA compounds, vectors, and transformants of the invention are merely illustrative and do not limit the scope of the invention. In addition, the substitution of GLN in place of ASN is illustrative and does not limit the scope of the invention as other substitutions, with the exception of CYS or PRO, could be used. Furthermore, skilled artisans will recognize that the various single amino acid substitutions of the present invention may be combined to create other novel zymogens.

All of the DNA compounds of the present invention were prepared by site-directed mutagenesis of the human protein C gene. The mutagenized zymogen-encoding molecules were then inserted into eukaryotic expression vectors such that expression of the zymogen genes was driven by the major late promoter of adenovirus-2. The vectors also comprise the P2 enhancer element of the BK virus positioned to enhance expression from the promoter. The vectors were transformed into *Escherichia coli* K12 AG1 cells and deposited and made part of the permanent stock culture collection of the Northern Regional Research Laboratories in Peoria, Ill. 61604 on Jan. 9, 1990. The specific cultures and accession numbers are found in Table II.

TABLE II

| Culture | Accession Number |
|---|---|
| E. coli K12 AG1/pLPC-Q097 | NRRL B-18608 |
| E. coli K12 AG1/pLPC-Q248 | NRRL B-18609 |
| E. coli K12 AG1/pLPC-Q313 | NRRL B-18610 |
| E. coli K12 AG1/pLPC-Q329 | NRRL B-18611 |

The cultures are obtained and the plasmids are isolated using conventional techniques, and then may be directly transfected into eukaryotic host cells for the production of the zymogen forms of human protein C. It is preferable to transform the plasmids into host cells which expresses the adenovirus E1A immediate-early gene product, in that the BK enhancer found on the vectors functions to enhance expression most efficiently in the presence of E1A. Skilled artisan will realize that a number of host cells express, or can be made to express, an immediate early gene product of a large DNA virus. Preferred cell lines are the human kidney 293 cell line (available from the American Type Culture Collection under accession number ATCC CRL 1573) or the Syrian Hamster cell line AV12-664 (ATCC 9595). Embryonic human kidney cell line 293 is most preferred.

To obtain even higher levels of expression, the genes encoding the various zymogen forms of protein C can be cut out of the deposited vectors and ligated into a vector which contains the GBMT transcription control unit. Specifically, plasmid pGT-h, which contains a hygromycin resistance conferring gene, can be obtained (in *E. coli* K12 AG1) from the NRRL under the accession number NRRL B-18592. The plasmid backbone is opened upon digestion of the plasmid with restriction enzyme BclI following isolation of plasmid DNA from a dam⁻ methylase strain of *E. coli*, such as GM48 (NRRL B-15725). The novel zymogen genes can each be removed from their respective plasmids via BclI digestion. The vector backbone is purified and dephosphorylated, then any of the novel zymogen genes of the present invention are ligated into the BclI site. The plasmids comprising the novel zymogen genes positioned for expression behind the GBMT transcription unit are then transformed into 293 cells, cultured and the novel zymogens can be purified from the culture by techniques which are well known in the art. One method for the purification of human protein C from cell culture is disclosed in Yan, U.S. patent application Ser. No. 07/139,281, Attorney Docket No. X-7309A, filed Aug. 16, 1989, the entire teaching of which is herein incorporated by reference. The GBMT transcription unit is described in more detail in Grinnell et al., U.S. patent application Ser. No. 07/484,082, Attorney Docket X-8084, filed herewith on even date, the entire teaching of which is herein incorporated by reference.

The compounds of the invention also include the zymogen forms generated upon secretion of the nascent proteins of the invention. Thus, the compounds of the invention include DNA coding sequences, expression vectors that drive expression of those sequences, nascent proteins produced upon translation of mRNA transcripts generated from those coding sequences, zymogens produced upon secretion of those nascent proteins, and activated derivatives of certain of the zymogens.

The DNA compounds of the invention can also be synthesized chemically, or by combining restriction fragments, or by a combination of techniques known in the art. DNA synthesizing machines are also available and can be used to construct the compounds of the invention.

The illustrative vectors of the invention, comprise the BK enhancer positioned to stimulate transcription by the adenovirus major late promoter of the coding sequence of the invention. Those skilled in the art recognize that a great number of eukaryotic promoters, enhancers, and expression vectors are known in the art and can be used in the method of the present invention. Those skilled in the art also recognize that a eukaryotic expression vector can function without an enhancer element. The key aspect of the present invention does not reside in the particular enhancer, if any, or promoter, used to drive expression of the protein C zymogen but rather resides in the novel coding sequence and corresponding proteins produced from that sequence.

However, choice of vector elements, such as promoters, enhancers, and selectable markers, can have great impact on the ultimate levels of protein produced by a eukaryotic host cell. U.S. patent application Ser. No. 849,999, filed Apr. 9, 1986, incorporated herein by reference, discloses a number of expression vectors for native zymogen protein C that utilize the BK enhancer to stimulate a eukaryotic promoter positioned to drive expression of nascent human protein C. These vectors drive especially high expression levels when transformed into eukaryotic cells that also express an immediate-early gene product of a large DNA virus, such as the E1A gene product of adenovirus. As is evident from the illustrative vectors pGT-Q097-h, pGT-Q248-h, pGT-Q313-h and pGT-329-h disclosed herein, the GBMT-E1A gene product expression method of Ser. No. 484,082 is especially preferred for use with the vectors of the present invention.

The present invention is not limited to use in a particular eukaryotic host cell. A variety of eukaryotic host cells are available from depositories such as the American Type Culture Collection (ATCC) Rockville, Md. 20852, and are suitable for use with the vectors of the invention. The choice of a particular host cell depends to some extent on the particular expression vector used to drive expression of the protein C-encoding DNA compounds of the invention. Because nascent human protein C and the nascent human protein C derivatives of the invention undergo substantial post-translational modification, however, some host cells are more preferred for use with the vectors of the invention. U.S. patent application Ser. No. 849,999 and Grinnell et al., 1987, Bio/Technology 5:1189 disclose that adenovirus-transformed, human embryonic kidney cells are especially preferred for use in the recombinant production of $\gamma$-carboxylated proteins such as human protein C. One such adenovirus-transformed, human embryonic kidney cell line is the 293 cell line, available from the ATCC under the accession number ATCC CRL 1573. The 293 cell line is also preferred for use with the vectors of the present invention.

However, the advantages of producing a $\gamma$-carboxylated protein, such as human protein C zymogen, in an adenovirus-transformed cell line are not limited to adenovirus-transformed human embryonic kidney cells. In fact, adenovirus-transformed cells in general are exceptional hosts for the production of $\gamma$-carboxylated human protein C. One especially preferred cell line of this type is the AV12-664 (hereinafter "AV12") cell line, available from the ATCC under the accession number ATCC CRL 9595. The AV12 cell line was constructed by injecting a Syrian hamster in the scruff of the neck with human adenovirus 12 and isolating cells from the resulting tumor. Example 3, below, describes the transformation of both the 293 and AV12 cell lines with illustrative vector pGT-Q097-h.

The vectors of the invention can be transformed into and expressed in a variety of eukaryotic, especially mammalian, host cells. Vectors of the invention that possess no selectable marker with which to isolate and identify stable eukaryotic transformants are useful not only for purposes of transient assay but also for purposes of cotransformation, a procedure disclosed in U.S. Pat. No. 4,399,216, issued Aug. 26, 1983, and incorporated herein by reference. The vectors of the invention can also comprise sequences that allow for replication in E. coli, as it is usually more efficient to prepare plasmid DNA in E. coli than in other host organisms.

Expression of the coding sequences for human protein C contained on the vectors of the invention occurs in those host cells in which the particular promoter associated with the structural gene functions. Exemplary host cells suitable for use in the invention are listed in Table III, along with appropriate comments.

TABLE III

| Host Cell | Origin | Source | Comments |
| --- | --- | --- | --- |
| HepG-2 | Human Liver Hepatoblastoma | *ATCC #HB 8065 | U.S. Pat. No. 4,393,133 describes the use of this cell line. |
| CV-1 | African Green Monkey Kidney | ATCC #CCL 70 | |
| LLC-MK$_2$ original | Rhesus Monkey Kidney | ATCC #CCL 7 | |
| LLC-MK$_2$ derivative | Rhesus Monkey Kidney | ATCC #CCL 7.1 | Grows faster than ATCC #CCL 7 |
| 3T3 | Mouse Embryo Fibroblasts | ATCC #CCL 92 | |
| CHO-K1 | Chinese Hamster Ovary | ATCC #CCL 61 | Proline-requiring. Derivatives of |

TABLE III-continued

| Host Cell | Origin | Source | Comments |
|---|---|---|---|
| | | | CHO-K1, such as the dhfr- derivative DXB11, can be generated from this host. |
| HeLa | Human Cervix Epitheloid | ATCC #CCL 2 | |
| RPMI8226 | Human Myeloma | ATCC #CCL 155 | IgG lambda-type light chain secreting |
| H4IIEC3 | Rat Hepatoma | ATCC #CRL 1600 | Derivatives, such as 8-azaguanine-resistant FAZA host cells, can be generated from this host. |
| C127I | Mouse Fibroblast | ATCC #CRL 1616 | |
| HS-Sultan | Human Plasma Cell Plasmocytoma | ATCC #CRL 1484 | |
| BHK-21 | Baby Hamster Kidney | ATCC #CCL 10 | |

*American Type Culture Collection, 12301 Parklaw Drive, Rockville, Maryland 20852-1776

As indicated by Table III, many mammalian host cells possess the necessary cellular machinery for the recognition and proper processing of the signal peptide on the nascent proteins of the invention and provide the post-translational modifications, such as glycosylation, γ-carboxylation, and β-hydroxylation, as are observed in human protein C present in blood plasma. However, as indicated above, optimal post-translational processing of HPC occurs in adenovirus-transformed cells. A wide variety of vectors, discussed below, exists for the transformation of such eukaryotic host cells, but the specific vectors exemplified below are in no way intended to limit the scope of the present invention.

The pSV2-type vectors comprise segments of the SV40 genome that constitute a defined eukaryotic transcription unit—promoter (ep), intervening sequence (IVS), and-polyadenylation (pA) site. In the absence of SV40 T-antigen, the plasmid pSV2-type vectors transform mammalian and other eukaryotic host cells by integrating into the host cell chromosomal DNA. A variety of plasmid pSV2-type vectors have been constructed (see *Eukaryotic Viral Vectors*, edited by Gluzman, published by Cold Spring Harbor Laboratories, Cold Spring Harbor, N.Y., 1982), such as plasmids pSV2-gpt, pSV2-neo, pSV2-dhfr, pSV2-hyg, and pSV2-β-globin, in which the SV40 promoter drives transcription of an inserted gene. These vectors are suitable for use with the coding sequences of the invention and are available either from the American Type Culture Collection (ATCC) in Rockville, Md. or from the Northern Regional Research Laboratory (NRRL) in Peoria, Ill.

Plasmid pSV2-dhfr (ATCC 37146) comprises a murine dihydrofolate reductase (dhfr) gene under the control of the SV40 earlypromoter. Under the appropriate conditions, the dhfr gene is known to be amplified, or copied, in the host chromosome. This amplification, described in a review article by Schimke, 1984, Cell 37:705–713, can involve DNA sequences closely contiguous with the dhfr gene, such as a nascent human protein C-encoding sequence of the invention, and thus can be used to increase production of the protein C zymogens of the invention.

Plasmids which were constructed for expression of the nascent protein C and protein C zymogens of the invention in mammalian and other eukaryotic host cells can utilize a wide variety of promoters. The present invention is in no way limited to the use of the particular eukaryotic promoters exemplified herein. Promoters such as the SV40 late promoter or the eukaryotic promoters disclosed in Bucher et al., 1986, Nuc. Acids Res. 14(24):1009, or promoters from eukaryotic genes, such as, for example, the estrogen-inducible chicken ovalbumin gene, the interferon genes, the glucocorticoid-inducible tyrosine aminotransferase gene, the thymidine kinase gene, and the major early and late adenovirus genes, can be readily isolated and modified for use on recombinant DNA expression vectors designed to produce human protein C zymogen in eukaryotic host cells. Eukaryotic promoters can also be used in tandem to drive expression of a coding sequence of the invention. Furthermore, a large number of retroviruses are known that infect a wide range of eukaryotic host cells. The long terminal repeats in the retrovirus DNA often encode promoter activity and thus can be used to drive expression of the coding sequences of the invention.

Plasmid pRSVcat (ATCC 37152) comprises portions of the long terminal repeat of the Rous Sarcoma virus (RSV), a virus known to infect chicken and other host cells. The RSV long terminal repeat sequences can be isolated on an ~0.76 kb NdeI-HindIII restriction fragment of plasmid pRSVcat. The promoter in the RSV long terminal repeat (Gorman et al., 1982, P.N.A.S. 79:6777) is suitable for use in vectors of the invention. Plasmid pMSVi (NRRL B-15929) comprises the long terminal repeats of the Murine Sarcoma virus (MSV), a virus known to infect mouse and other host cells. These repeat sequences are suitable for use as a promoter in the vectors of the invention. The mouse metallothionein (MMT) promoter has also been well characterized for use in eukaryotic host cells and is suitable for use in the vectors of the invention. The MMT promoter is present in the 15 kb plasmid pdBPV-MMTneo (ATCC 37224), which can serve as the starting material for the construction of other plasmids of the present invention.

Many modifications and variations of the present illustrative DNA sequences and plasmids are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or DNA sequence of human protein C and can be constructed by following conventional synthetic or sitespecific mutagenesis procedures. Synthetic methods can be carried out in substantial accordance with the procedures of Itakura et al., 1977 Science 198:1056 and Crea et al., 1978, Proc. Nat. Acad. Sci. USA 75:5765. Therefore, the present invention is in no way limited to the DNA sequences and plasmids specifically exemplified.

After transformation of a vector of the invention into a eukaryotic host cell, one can select transformants on the basis of a selectable phenotype. This selectable phenotype can be conferred either by a selectable marker present on the expression vector or present on another vector cotransformed with the expression vector into the host cell. Once transformants are selected, it is desirable to identify which transformants are expressing the highest levels of the desired protein encoded on the expression vector. Such identification is especially important after a cotransformation procedure, which generates a number of transformants that contain only the plasmid containing the selectable marker and so do not contain the expression vector. In Example 4, below, a protocol not only for identifying cells that express and secrete a desired protein but also for quantifying, relative to the other cells examined using the method, the amount of protein secreted is described. The protocol also allows for the isolation of viable cells secreting the highest levels of a desired protein.

Methods for the activation of zymogen forms of human protein C to activated protein C (APC) are old and well known in the art. Protein C may be activated by thrombin alone, by a thrombin/thrombomodulin complex, by Russell's Viper venom or by a variety of other means. The activity of human protein C zymogens may be measured following thrombin activation by either total amidolytic assays or by anticoagulation assays. Thrombin activation and protein C assays (amidolytic and anticoagulant) were performed according to the teaching of Grinnell et al., 1987, *Biotechnology* 5:1187–1192, the entire teaching of which is herein incorporated by reference. The specific amidolytic activities of human protein C carbohydrate mutants are disclosed in Table IV.

TABLE IV

| APC Form | Amidolytic Activity (U/mg) | % Antcoagulant Activity[a] | Relative level of functional activity[c] |
|---|---|---|---|
| Native APC | 32 ± 10 | 119 ± 24 | 1 |
| Q097 | 80 ± 10 | 118 ± 11 | 2.5 |
| Q248 | ND[b] | ND | ND |
| Q313 | 52 ± 8 | 98 ± 8 | 1.4 |
| Q329 | 116 ± 16 | 128 ± 21 | 3.9 |

[a]Determined by dividing the quantity of activated protein C determined by APTT assay by the quantity determined by amidolytic assay.
[b]Not Done
[c]relative amidolytic activity, compared to native APC, times the relative anticoagulant activity.

The zymogen molecules used in the assays of Table IV were quantitated by an ELISA assay using monoclonal antibodies which may not have reacted with the mutants or derivatives to the same extent as the wild type molecule from which the antibodies were raised. Consequently, further purification and quantitation based upon protein content led to the data portrayed in Table V.

TABLE V

| | Functional Activity (units/mg) | |
|---|---|---|
| HPC | Amidolytic (relative to wtHPC) | Anticoagulant (relative to plasma wtHPC) |
| plasma-derived | nd | 250 (1) |
| wt aPC | 35 ± 5 (1) (n = 7) | 325 ± 65 (1.3) (n = 5) |
| Q097 | 32 ± 4 (0.9) (n = 10) | 303 ± 33 (1.2) (n = 3) |
| Q248 | 63 ± 12 (1.8) (n = 8) | 669 ± 172 (2.7) (n = 3) |
| Q313 | 52 ± 7 (1.5) (n = 9) | 627 ± 99 (2.5) (n = 3) |
| Q329 | 47 ± 6 (1.4) (n = 9) | 516 ± 29 (2.1) (n = 3) |

The first number in parentheses is the fold increase in activity over plasma-derived HPC. The number of independent samples (n) determined in duplicate or triplicate is indicated.

In addition to the enhanced anticoagulant activity of the derivatives set forth in Table V, the mutant Q313 displayed an increased affinity for thrombin, resulting in an approximately three fold increase in the rate of activation by thrombin alone or in complex with the cofactor thrombomodulin. This increase in rate is useful in creating a more susceptible zymogen form of protein C for clinical use and also in improving the production process for cleavage of zymogen protein C to make activated protein C. The kinetic parameter of activation of zymogen Q313 are shown in Table VI.

TABLE VI

| Substrate | $K_m$ (uM) | $k_{cat}$ (min$^{-1}$) | $k_{cat}/K_m$ (min$^{-1}$mM$^{-1}$) |
|---|---|---|---|
| wt HPC | 6.1 ± 0.45 n = 3 | 480 ± 14 | 79 |
| Q313 | 1.9 ± 0.50 n = 4 | 380 ± 14 | 200 |

Activated protein C has substantial anti-thrombotic properties in the prevention of extension of intravenous thrombi, in the prevention of formation of arterial thrombi, and in the prevention of death and organ failure from Gram negative sepsis, endotoxemia, and disseminated intravascular coagulation. Of particular importance, the increased functional activity of the activated protein C derivatives of the invention will allow for reduced dosages in the above clinical indications with potential increased margin of safety.

The activated recombinant protein C zymogens of the invention are useful in the prevention and treatment of a wide variety of acquired disease states involving intravascular coagulation, including deep vein thrombosis, pulmonary embolism, peripheral arterial thrombosis, emboli originating from the heart or peripheral arteries, acute myocardial infarction, thrombotic strokes, and disseminated intravascular coagulation. These protein C derivatives can also be used efficiently in the treatment of the significant numbers of patients with heterozygous protein C deficiencies presenting recurrent deep vein thrombosis and in the case of the homozygous protein C deficient patients with purpura fulminans. An attractive therapeutic indication for activated protein C is the prevention of deep vein thrombosis and pulmonary embolism currently treated with low doses of heparin.

Similarly, the protein C derivatives of the invention can be used for the treatment of emboli originating from thrombi in peripheral arteries, most notably the carotid arteries, which are not treated or prevented satisfactorily with currently used regimens, which include drugs capable of suppressing platelet function, oral anticoagulants, or combinations thereof.

The activated derivatives of the invention will also be useful in treating acute myocardial infarction, because of their pro-fibrinolytic properties, once activated. These activated derivatives can be given with tissue plasminogen activator during the acute phases of the myocardial infarction. After the occluding coronary thrombus is dissolved, the activated derivatives can be given for additional days to prevent acute myocardial reinfarction.

Activated protein C is useful in the treatment of disseminated intravascular coagulation. Heparin and the oral anticoagulants have been given to patients with disseminated intravascular coagulation (DIC) in extensive clinical trials, but the results have been disappointing. In disseminated intravascular coagulation, activated protein C, as well as the activated derivatives of the present invention, has a distinct advantage over conventional anticoagulants.

Conventional anticoagulant drugs, particularly warfarin, are useful in the treatment of invasive malignant tumors. Many tumor cells produce substances which trigger the activation of the coagulation system resulting in local fibrin deposits. These fibrin deposits function as "nests" in which cancer cells can divide to form metastatic lesions. However, it is not possible to administer warfarin or other conventional anticoagulants in combination with the more intensive and effective forms of chemotherapy, because such therapy always produces a sharp drop in the platelet count, and thrombocytopenia combined with warfarin therapy puts the patient at an unacceptably high risk for serious bleeding complications. The protein C derivatives of the invention, like activated protein C, being more selective than conventional anticoagulants and having a far higher therapeutic index than either heparin or the oral anticoagulants, can be given relatively safely to the thrombocytopenic patient, thus making possible the treatment of patients with invasive cancers with effective and intensive chemotherapy in combination with an activated protein C derivative of the invention.

The zymogens, and activated counterparts, of the present invention can be formulated according to known methods to prepare pharmaceutically useful compositions, whereby a human protein C zymogen or activated protein C of the invention is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences* 16th ed., 1980, Mack Publishing Co., edited by Osol et al., which is hereby incorporated by reference. Such compositions will contain an effective amount of a protein C zymogen, or activated counterpart, together with a suitable amount of carrier vehicle to prepare pharmaceutically acceptable compositions suitable for effective administration to the host. The protein C composition can be administered parenterally, or by other methods that ensure its delivery to the bloodstream in an effective form.

The following Examples illustrate the methods and describe the construction protocols for representative compounds, vectors and transformants of the invention without limiting the same thereto.

EXAMPLE 1

Isolation of Plasmid pLPC-O097

Lyophils of *E. coli* K12 AG1/pLPC-Q097 are obtained from the Northern Regional Research Laboratory, Peoria, Ill. 61604, under the accession number NRRL B-18608. The lyophils are decanted into tubes containing 10 ml LB medium (10 g Bacto-tryptone, 5 g Bacto-yeast extract, and 10 g NaCl per liter; pH is adjusted to 7.5) and incubated two hours at 32° C., at which time the cultures are made 50 µg/ml in ampicillin and then incubated at 37° C. overnight.

A small portion of the overnight culture is placed on LB-agar (LB medium with 15 g/l Bacto-agar) plates containing 50 µg/ml ampicillin in a manner so as to obtain a single colony isolate of *E. coli* K12 AG1/pLPC-Q097. The single colony obtained was inoculated into 10 ml of LB medium containing 50 µg/ml ampicillin and incubated overnight at 37° C. with vigorous shaking. The 10 ml overnight culture was inoculated into 500 ml LB medium containing 50 µg/ml ampicillin and incubated at 37° C. with vigorous shaking until the culture reached stationary phase.

The following procedure is adapted from Maniatis et al., 1982, *Molecular cloning* (Cold Spring Harbor Laboratory).

The cells were harvested by centrifugation at 4000 g for 10 minutes at 4° C., and the supernatant was discarded. The cell pellet was washed in 100 ml of ice-cold STE buffer (0.1M NaCl; 10 mM Tris-HCl, pH 7.8; and 1 mM EDTA). After washing, the cell pellet was resuspended in 10 ml of Solution 1 (50 mM glucose; 25 mMTris-HCl, pH 8.0; and 10 mM EDTA) containing 5 mg/ml lysozyme and left at room temperature for 10 minutes. Twenty ml of Solution 2 (0.2N NaOH and 1% SDS) were then added to the lysozyme-treated cells, and the solution was gently mixed by inversion. The mixture was incubated on ice for 10 minutes.

Fifteen ml of ice-cold 5M potassium acetate, pH 4.8, were added to the lysed-cell mixture and the solution mixed by inversion. The solution was incubated on ice for 10 minutes. The 5M potassium acetate solution was prepared by adding 11.5 ml of glacial acetic acid to 28.5 ml of water and 60 ml of 5M potassium acetate; the resulting solution is 3M with respect to potassium and 5M with respect to acetate.

The lysed cell mixture was centrifuged in a Beckman SW27 (or its equivalent) at 20,000 rpm for 20 minutes at 4° C. The cell DNA and debris formed a pellet on the bottom of the tube. About 36 ml of supernatant were recovered, and 0.6 volumes of isopropanol were added, mixed, and the resulting solution left at room temperature for 15 minutes. The plasmid DNA was collected by centrifugation at 12,000 g for 30 minutes at room temperature. The supernatant was discarded, and the DNA pellet was washed with 70% ethanol at room temperature. The ethanol wash was decanted, and the pellet was dried in a vacuum desiccator. The pellet was then resuspended in 8 ml of TE buffer (10 mM Tris-HCl, pH 8.0, and 1 mM EDTA).

Eight grams of CsCl were added to the DNA solution. About 0.8 ml of a 10 mg/ml solution of ethidium bromide in water were added for each 10 ml of CsCl-DNA solution. The final density of the solution was about 1.55 g/ml, and the ethidium bromide concentraton was about 600 µg/ml. The solution was transferred to a Beckman Type 50 centrifuge tube, filled to the top with paraffin oil, sealed, and centrifuged at 45,000 rpm for 24 hours at 20° C. After centrifugation, two bands of DNA were visible in ordinary light. After removing the cap from the tube, the lower DNA band was removed by using a syringe with a #21 hypodermic needle inserted through the side of the centrifuge tube.

The ethidium bromide was removed by several extractions with water-saturated 1-butanol. The CsCl was removed by dialysis against TE buffer. After extractions with buffered phenol and then chloroform, the DNA was precipitated, washed with 70% ethanol, and dried. About 1 mg of plasmid pLPC-Q097 was obtained and stored at 4° C. in TE buffer at a concentration of about 1 µg/l. A restriction site and function map of plasmid pLPC-Q097 is presented in FIG. 1 of the accompanying drawings. In the same manner, plasmids pLPC-Q248, pLPC-Q313, and pLPC-Q329 are isolated from their corresponding host cells, also available from the NRRL. Restriction site and function maps of each of these plasmids are presented in the accompanying drawings.

EXAMPLE 2 construction of Plasmid pGT-097-h

Plasmids pLPC-Q097, pLPC-Q248, pLPC-Q313, and pLPC-Q329 may be directly transformed into eukaryotic host cells (preferably 293 cells) for the production of high levels of human protein C zymogens. Even higher levels of expression and secretion of product may be obtained if the gene encoding the mutant zymogen is ligated into a vector such that the expression of the gene is driven by the GBMT transcription unit. The GBMT transcription unit is fully described in Grinnell et al., U.S. patent application Ser. No. 07/484,082, Attorney Docket No. X-8084, filed herewith on even date, the entire teaching of which is herein incorporated by reference.

Plasmid pGTC is one such vector, wherein the wild type human protein C zymogen gene is driven by the GBMT transcription unit. The wild type protein C gene can be easily removed from the vector on a BclI restriction fragment and any of the genes of the present invention can be inserted into the vector on a BclI restriction fragment. Digestion of plasmid DNA with BclI is inhibited by methylation at adenine in the sequence 5'-GATC-3'. Therefore, plasmid pGTC was prepared from E. coli host cells that lack an adenine methylase, such as that encoded by the dam gene, the product of which methylates the adenine residue in the sequence 5'-GATC-3'. E. coli K12 GM48 (NRRL B-15725) lacks a functional dam methylase and so is a suitable host to use for the purpose of preparing plasmid pGTC DNA for use as starting material in the construction of derivative plasmids.

E. coli K12 GM48 cells were cultured and made competent for transformation, and plasmid pGTC was used to transform the E. coli K12 GM48 cells in substantial accordance with the procedure of Example 1. The transformed cells were plated on L-agar containing ampicillin, and once the ampicillin-resistant, E. coli K12 GM48/pGTC transformants had formed colonies, one such colony was used to prepare plasmid pGTC DNA in substantial accordance with the procedure of Example 1. About 1 mg of plasmid pGTC DNA was obtained and suspended in about 1 ml of TE buffer. This procedure was used for preparing plasmid DNA from pGT-h and pGT-d. Plasmid pGT-d comprises the GBMT transcription unit with no gene at the BclI site, so that any gene can be easily inserted. Plasmid pGT-d also comprises the murine dhfr gene so that any transformant can be selected or amplified using the methotrexate resistance phenotype. Plasmid pGT-h comprises the GBMT transcription unit, a BclI site for easy insertion of a gene of interest and the hygromycin resistance-conferring gene. E coli K12 AG1 strains comprising each of these plasmids were deposited with the NRRL on January 18, 1990. The strains are available under the accession numbers NRRL B-18591 (for E. coli K12 AB1/pGT-d), NRRL B-18592 (for E. coli K12 AG1/pGT-h), and NRRL B-18593 (for E. coli K12 AG1/pGTC). Restriction site and function maps of these plasmids are presented in the accompanying drawings.

About 10 µl of the plasmid pLPC-Q097 DNA prepared from GM48 cells are mixed with 20 µl 10×BclI restriction buffer (100 mM Tris-HCl (pH 7.4), 1.5M KCl, 100 mM $MgCl_2$ and 10 mM DTT), 20 µl 1 mg/ml BSA, 5 µl restriction enzyme BclI (~50 Units, as defined by Bethesda Research Laboratories (BRL), from which all restriction enzymes used herein are obtained), and 145 µl of water, and the resulting reaction is incubated at 37° C. for 2 hours. Restriction enzyme reactions described herein are routinely terminated by phenol and then chloroform extractions, which are followed by precipitation of the DNA, an ethanol wash, and resuspension of the DNA in TE Buffer. The digested DNA is then electrophoresed through a 1% agarose prep gel and the about 1400 base pair restriction fragment comprising the mutant gene is purified using a BioRad Prep-A-Gene Kit, according to the manufacturer's instructions.

Plasmid pGT-h is then isolated from E. coli K12 AG1/pGTC (NRRL B-18592) in substantial accordance with the teaching of Example 1 and propagated in GM48 and isolated as in substantial accordance with the teaching of Example 2. Plasmid pGT-h DNA is then digested with restriction enzyme BclI as taught above, then the large vector fragment is isolated and purified. This vector fragment is brought up to 90 µl volume with TE (pH 8.0), then 10 µl (0.05 Unit) of Calf Intestine Alkaline Phosphatase is added to dephosphorylate the vector ends. The mixture is incubated at 37° C. for 30 minutes, then 10 µl of 500 mM EGTA is added and the reaction is incubated at 65° C. for 45 minutes to inactivate the enzyme. The reaction is then phenol/chloroform extracted, ethanol precipitated, washed and resuspended in 20 µl of water.

About 7 µl (10 ng) of the BclI-digested vector backbone is then mixed with about 1 µl (100 mg) of the about 1400 base pair BclI restriction fragment of plasmid pLPC-Q097, 1 µl 10X ligase buffer (0.5M Tri-HCl (pH 7.6), 100 $mMMgCl^2$, 100 mMDTT and 500 µg/ml BSA) and 1 µl T4 DNA ligase. The ligation reaction is then incubated for 12 to 16 hours at 16° C. The ligation reaction can lead to plasmids which contain the mutant zymogen gene oriented for transcription from the GBMT transcription unit, or plasmids wherein the gene is ligated in the opposite direction. Those plasmids which contain the gene in the proper orientation for transcription are designated plasmid pGT-Q097-h.

Frozen competent E. coli K12 AG1 cells are obtained from Strategene, 3770 Tansey Road, San Diego, Calif. 92121. About 5 µl of the ligation reaction is mixed with a 100 µl aliquot of competent cells, then the cell-DNA mixture is incubated on ice for one hour, heat-shocked at 42° C. for 45 seconds, then chilled on ice for about 2 minutes. The cell-DNA mixture is diluted into 1 ml of SOC media in Falcon 2059 tubes and incubated at 37° C. for one hour. One hundred microliter aliquots are plated on LB-agar plates containing ampicillin and incubated at 37° C. until colonies appear.

The colonies are individually cultured, and the plasmid DNA of the individual colonies is examined by restriction enzyme analysis. Plasmid DNA isolation is performed on a smaller scale in accordance with the procedure of Example 1, but the CsCl step is omitted until the proper E. coli K12 AG1/pGT-Q097-h transformants are identified. At that time, a large scale, highly purified plasmid prep is performed. Following the teaching of Examples 1 and 2, any of the mutant zymogen genes can easily be cloned into any of the GBMT vectors to form plasmids pGT-Q097-h, pGT-Q248-h, pGT-Q313-h and pGT-Q329-h.

EXAMPLE 3

Construction of Adenovirus-transformed Human Embryonic Kidney Cell Line 293 and Adenovirus-transformed Syrian Hamster Cell Line AV12 Transformants Using Plasmid pGT-097-h Human Embryonic Kidney Cell Line 293 is available from the American Type Culture Collection under the accession number ATCC CRL 1573. The adenovirus-transformed Syrian hamster cell line AV12 is also available from the American Type Culture Collection under the accession number ATCC CRL 9595. The transformation procedure described below refers to 293 cells as the host cell line; however, the procedure is generally applicable to most eukaryotic cell lines, including the AV12 cell line, and to the expression vectors of the invention.

293 cells are obtained from the ATCC under the accession number CRL 1573 in a 25 mm² flask containing a confluent monolayer of about 5.5×10⁶ cells in Eagle's Minimum Essential Medium (Gibco) with 10% heat-inactivated horse serum. The flask is incubated at 37° C.; medium is changed twice weekly. Media is composed of DMEM (Gibco) supplemented with 10% fetal calf serum, 50 µg/ml gentamicin, and 10 µg/ml AquaMEPHYTON® phytonadione vitamin $K_1$ (Merck Sharp and Dohme, Merck and Co., Inc., West Point, PA 19486). The cells are subcultured by removing the medium, rinsing with Hank's Balanced Salts solution (Gibco), adding 0.25% trypsin (containing 0.2 g/L EDTA) for 1–2 minutes, rinsing with fresh medium, aspirating, and dispensing into new flasks at a subcultivation ratio of 1:5 or 1:10.

One day prior to transformation, cells are seeded at 0.7×10⁶ cells per 100 mm dish. Sterile, ethanol-precipitated plasmid DNA dissolved in TE buffer is used to prepare a 2×DNA-$CaCl_2$ solution containing 25 µg/ml of the transforming plasmid DNA and 250 mM $CaCl_2$. 2XHBSS is prepared containing 280 mM NaCl, 50 mMHepes, and 1.5 mM sodium phosphate, with the pH adjusted to 7.05–7.15. The 2×DNA-$CaCl_2$ solution is added dropwise to an equal volume of sterile 2×HBSS. A one ml sterile plastic pipette with a cotton plug is inserted into the mixing tube that contains the 2X HBSS, and bubbles are introduced by blowing while the DNA is being added. The calcium-phosphate-DNA precipitate is allowed to form without agitation for 30–45 minutes at room temperature.

The precipitate is then mixed by gentle pipetting with a plastic pipette, and one ml (per plate) of precipitate is added directly to the 10 ml of growth medium that covers the recipient cells. After 4 hours of incubation at 37° C., the media is replaced with fresh media and the cells allowed to incubate for an additional 72 hours before providing selective pressure. For plasmids that do not comprise a selectable marker that functions in eukaryotic cells the transformation procedure utilizes a mixture of plasmids: the expression vector of the present invention that lacks a selectable marker; and an expression vector that comprises a selectable marker that functions in eukaryotic cells. A variety of vectors are available for use in such cotransformation systems and include plasmids pSV2-dhfr (ATCC 37146), pSV2-neo (ATCC 37149), pSV2-gpt (ATCC 37145), and pSV2-hyg (NRRL B-18039). Plasmid pSV2-hyg confers resistance to hygromycin B to eukaryotic host cells. This co-transformation technique allows for the selection of cells that contain the plasmid with the selectable marker. These cells are further examined to identify cells that comprise both of the transforming plasmids. Of course, the present invention also comprises expression vectors that contain a selectable marker for eukaryotic cells and thus do not require use of the cotransformation technique.

For cells transfected with plasmids containing the hygromycin resistance-conferring gene such as plasmid pGT-Q097-h, hygromycin B is added to the growth medium to a final concentration of about 200 µg/ml. The cells are then incubated at 37° C. for 2–4 weeks with medium changes at 3 to 4 day intervals. The resulting hygromycin-resistant colonies are transferred to individual culture flasks for characterization. Plasmid pSV2-neo confers resistance to neomycin (G418 is also used in place of neomycin), and selection of G418-resistant colonies is performed in substantial accordance with the selection procedure for hygromycinresistant cells, except that G418 is added to a final concentration of 300 µg/ml.

The use of the dihydrofolate reductase (dhfr) gene or the methotrexate resistance-conferring derivative of the dhfr gene (dhfr-mtx) as a selectable marker for introducing a gene or plasmid into a dhfr-deficient cell line and the subsequent use of methotrexate to amplify the copy number of the plasmid has been well established in the literature. 293 cells are dhfr positive, so 293 transformants that contain plasmids comprising the dhfr gene are not selected solely on the basis of the dhfr-positive phenotype, which is the ability to grow in media that lacks hypoxanthine and thymine. Cell lines that do lack a functional dhfr gene and are transformed with dhfr-containing plasmids can be selected for on the basis of the dhfr+ phenotype. Although the use of dhfr as a selectable and amplifiable marker in dhfr-producing cells has not been well studied, evidence in the literature would suggest that dhfr can be used as a selectable marker and for gene amplification in dhfr-producing cells. The present invention is not limited by the selectable marker used on expression vectors. Moreover, amplifiable markers such as metallothionein genes, adenosine deaminase genes, or members of the multigene resistance family, exemplified by the P-glyco-protein gene, can be utilized.

Transformation of the 293 cell line with plasmids pGT-Q097-h, pGT-Q248-h, pGT-Q313-h and pGT-Q329-h yielded a number of transformants. These transformants were analyzed as described in Example 4.

EXAMPLE 4

Selection of Cells Secreting Human Protein C Zymogen Mutants

The hygromycin-resistant transformants obtained in Example 3 are grown on 100 mm² tissue culture dishes at a density of several hundred cell clones per tissue culture dish. The media is decanted, and the cells are rinsed twice with 5 ml aliquots of Hank's Balanced salt solution (Gibco). A solution of sterile 0.45% agar (Sigma Type 4 agarose, catalogue #A3643, Sigma Chemical Co., P.O. Box 14508, St. Louis, Mo. 63178) is prepared by mixing 1 ml of 1.8% agar (47° C.) with 3 ml of Dulbecco's Modified Eagle's (DME) Salts (Gibco) (37° C.), and 2 ml of this 0.45% agar solution are layered over the cells.

Nitrocellulose filters (Schleicher and Schuell, Inc., Keene, N.H. 03431) are boiled and then autoclaved 2 hours to remove the wetting agent, which is toxic to the cells. The filters are then placed on top of the agar layer, and after air bubbles are removed, the plates are incubated at 37° C. for 1 to 3 hours. The filters, previously marked to indicate the original orientation of the filter on the dish so as to facilitate later identification of colonies, are then removed and placed in PBS (50 mM Tris-HCl, pH=7.2, and 150 mM NaCl).

To keep the cells on the dish viable during analysis of the filters, the cells are overlayed with 8 ml of a mixture containing 2 ml of 1.8% agar (47° C.), 2 ml of DME salts (37° C.), and 4 ml of DME salts with 20% fetal bovine serum (37° C.). The cells are then placed in a 37° C. incubator.

All washes and reactions carried out on the filters are accomplished while the filters are on a rocking platform. The filters are first blocked by incubation at room temperature in 5% milk in PBS. The filters are then rinsed (5 minutes/rinse) four times in PBS. A 10 µg/ml biotinylated goat anti-human protein C polyclonal antibody in 2.5% bovine serum albumin is added to the filter (in sufficient quantities to cover the filter), which is then incubated at 37° C. for 1 hour.

Purification of protein C, for subsequent use to prepare antibody against protein C, can be accomplished as described by Kisiel, 1979, J. Clin. Invest. 64:761. Polyclonal antibody can be prepared by the procedure disclosed in *Structural Concepts in Immunology and Immunochemistry* by E. A. Kabat, published in 1968 by Holt, Rhinehart, and Winston. Monoclonal antibody, which is also suitable for use in the assay, can be prepared as disclosed in Kohler and Milstein, 1975, Nature, 256:495, or as disclosed in U.S. Pat. No. 4,696,895; EPO Pub. No. 205046; Laurell et al., 1985, FEBS 191(1):75; Suzuki et al., 1985, J. Biochem. 97:127–138; and EPO Pub. No. 138222. The avidin D and biotinylated horse radish peroxidase (HRP) used in the assay are obtained in a rectastain™ kit (Vector Laboratories, Inc., 30 Ingold Road, Burlingame, Calif. 94010). Biotin is also obtained from Vector Laboratories, Inc.

The filters are rinsed four times with PBS at 4° C. Then, avidin D and biotinylated horse radish peroxidase are prepared and added as per the manufacturer's instructions in the Vectastain™ (Vector Laboratories) kit. The filters are incubated with the E-conjugated avidin D for 1 hour at 4° C. (longer incubation times, i.e., overnight, can be used when small amounts of protein are being secreted); then, the filters are rinsed four times with PBS at 4° C.

To develop the indicator color on the filters, about 30 mg of HRP color-development reagent (4-chloro-1 -napthol, Sigma) dissolved in ice-cold 100% methanol are added to 50 ml of PBS and 30 µl of 30% $H_2O_2$. This mixture is added to the nitrocellulose filters, which are incubated at room temperature until the color develops. Colonies secreting the most human protein C zymogen of the invention will be indicated on the filters not only by earliest appearance of the color but also by darker spots on the filter.

After the filters have been developed, the filters are again realigned with the original plates to determine which colonies are associated with which spots on the filter. The colonies secreting the most human protein C zymogen of the invention are then selected and used for production of the zymogen.

Those skilled in the art will recognize that the above assay is merely illustrative of the method of identifying high secreting cell lines. A variety of assay procedures can be successfully employed in the method. For instance, a double-antibody reaction can be employed in which the biotinylated goat anti protein C antibody is replaced with a goat anti-protein C antibody (IgG) and a biotinylated anti-goat IgG antibody.

The zymogen mutants may be purified from the cell cultures. The supernatant is removed from cells expressing the recombinant product and purified on a Pharmacia Fast-flow-Q column. About 1 ml of the resin is equilibrated with 20 mM Tris-HCl (pH 7.4), 0.15M NaCl, 5 mM EDTA, 4 mM benzamidine. The culture supernatant is brought to pH 7.4 by the addition of Tris-HCl (pH 8.0) and 5 mM EDTA, 4 mM Benzamidine. The supernatant is loaded onto the resin in a column and washed with three column volumes of Tris-HCl (pH 7.4), 0.15M NaCl, 5 mM EDTA followed by 3 column volumes of 20 mM Tris (HCl), 0.15M NaCl, 4 mM benzamidine. The recombinant product is eluted from the column using an elution buffer containing 10 mM $CaCl_2$ in 20 mM Tris-HCl (pH 7.4), 0.15M NaCl, 5 mM benzamidine.

Specific activity of the product is determined according to the procedure of Grinnell et al., (1987), *Biotechnology* 5:1189–1192 as follows: concentrated and dialyzed product from the column eluate is first activated with an immobilized thrombin-thrombomodulin complex, then the amidolytic activity of the product was measured by the hydrolysis of a tripeptide substrate S-2366 (obtained from Helena Labs). The anticoagulant activity of the product is determined by the prolongation of an activated partial thromboplastin time using reagents from Helena.

We claim:

1. A recombinant DNA compound comprising a coding sequence for a protein, said protein comprising, from the amino terminus to the carboxy terminus, the amino acid sequence:

METTRPGLNLEUTHRSERLEULEULEU
PHEVALALATHRTRPGLYILESERGLY
THRPROALAPROLEUASPSERVALPHE
SERSERSERGLUARGALAHISGLNVAL
LEUARGILEARGLYSARGALAASNSER
PHELEUGLUGLULEUARGHISSERSER
LEUGLUARGGLUCYSILEGLUGLUILE
CYSASPPHEGLUGLUALALYSGLUILE
PHEGLNASNVALASPASPTHRLEUALA
PHETRPSERLYSHISVALASPGLYASP
GLNCYSLEUVALLEUPROLEUGLUHIS
PROCYSALASERLEUCYSCYSGLYHIS
GLYTHRCYSILEASPGLYILEGLYSER
PHESERCYSASPCYSARGSERGLYTRP
GLUGLYARGPHECYSGLNARGGLUVAL
SERPHELEUASNCYSSERLEUASPASN
GLYGLYCYSTHRHISTYRCYSLEUGLU
GLUVALGLYTRPARGARGCYSSERCYS
ALAPROGLYTYRLYSLEUGLYASPASP
LEULEUGLNCYSHISPROALAVALLYS
PHEPROCYSGLYARGPROTRPLYSARG
METGLULYSLYSARGSERHISLEULYS
ARGASPTHRGLUASPGLNGLUASPGLN
VALASPPROARGLEUILEASPGLYLYS
METTHRARGARGGLYASPSERPROTRP
GLNVALVALLEULEUASPSERLYSLYS
LYSLEUALACYSGLYALAVALLEUILE
HISPROSERTRPVALLEUTHRALAALA
HISCYSMETASPGLUSERLYSLYSLEU
LEUVALARGLEUGLYGLUTYRASPLEU
ARGARGTRPGLULYSTRPGLULEUASP
LEUASPILELYSGLUVALPHEVALHIS
PROASNTYRSERLYSSERTHRTHRASP
ASNASPILEALALEULEUHISLEUALA
GLNPROALATHRLEUSERGLNTHRILE
VALPROILECYSLEUPROASPSERGLY
LEUALAGLUARGGLULEUASNGLNALA
GLYGLNGLUTHRLEUVALTHRGLYTRP
GLYTYRHISSERSERARGGLULYSGLU
ALALYSARGGLNARGTHRPHEVALLEU
ASNPHEILELYSILEPROVALVALPRO
HISASNGLUCYSSERGLUVALMETSER
ASNMETVALSERGLUASNMETLEUCYS
ALAGLYILELEUGLYASPARGGLNASP
ALACYSGLUGLYASPSERGLYGLYPRO
METVALALASERPHEHISGLYTHRTRP
PHELEUVALGLYLEUVALSERTRPGLY
GLUGLYCYSGLYLEULEUHISASNTYR
GLYVALTYRTHRLYSVALSERARGTYR
LEUASPTRPILEHISGLYHISILEARG
ASPLYSGLUALAPROGLNLYSSERTRP
ALAPRO—COOH.

2. A method for the recombinant production of a zymogen form of human protein C upon secretion from a eukaryotic host cell, said method comprising the steps of:

(A) transforming a eukaryotic host cell with a recombinant DNA vector, said vector comprising,
  (i) a DNA sequence that encodes an amino acid sequence, said amino acid residue sequence comprising from, the amino terminus to the carboxy terminus, the amino acid sequence:

| | | | | | | | | | | | | | | | |
|---|---|---|---|---|---|---|---|---|---|---|---|---|---|---|---|
| MET | TRP | GLN | LEU | THR | SER | LEU | LEULEU | PHE | VAL | ALA | THR | TRP | GLY | ILE |
| SER | GLY | THR | PRO | ALA | PRO | LEU | ASPSER | VAL | PHE | SER | SER | SER | GLU | ARG |
| ALA | HIS | GLN | VAL | LEU | ARG | ILE | ARG LYS | ARG | ALA | ASN | SER | PHE | LEU | GLU |
| GLU | LEU | ARG | HIS | SER | SER | LEU | GLUARG | GLU | CYS | ILE | GLU | GLU | ILE | CYS |
| ASP | PHE | GLU | GLU | ALA | LYS | GLU | ILEPHE | GLN | ASN | VAL | ASP | ASP | THR | LEU |
| ALA | PHE | TRP | SER | LYS | HIS | VAL | ASPGLY | ASP | GLN | CYS | LEU | VAL | LEU | PRO |
| LEU | GLU | HIS | PRO | CYS | ALA | SER | LEUCYS | CYS | GLY | HIS | GLY | THR | CYS | ILE |
| ASP | GLY | ILE | GLY | SER | PHE | SER | CYSASP | CYS | ARG | SER | GLY | TRP | GLU | GLY |
| ARG | PHE | CYS | GLN | ARG | GLU | VAL | SERPHE | LEU | ASN | CYS | SER | LEU | ASP | ASN |
| GLY | GLY | CYS | THR | HIS | TYR | CYS | LEUGLU | GLU | VAL | GLY | TRP | ARG | ARG | CYS |
| SER | CYS | ALA | PRO | GLY | TYR | LYS | LEUGLY | ASP | ASP | LEU | LEU | GLN | CYS | HIS |
| PRO | ALA | VAL | LYS | PHE | PRO | CYS | GLYARG | PRO | TRP | LYS | ARG | MET | GLU | LYS |
| LYS | ARG | SER | HIS | LEU | LYS | ARG | ASPTHR | GLU | ASP | GLN | GLU | ASP | GLN | VAL |
| ASP | PRO | ARG | LEU | ILE | ASP | GLY | LYSMET | THR | ARG | GLY | ASP | SER | PRO | |
| TRP | GLN | VAL | VAL | LEU | LEU | ASP | SERLYS | LYS | LYS | LEU | ALA | CYS | GLY | ALA |
| VAL | LEU | ILE | HIS | PRO | SER | TRP | VALLEU | THR | ALA | ALA | HIS | CYS | MET | ASP |
| GLU | SER | LYS | LYS | LEU | LEU | VAL | ARG LEU | GLY | GLU | TYR | ASP | LEU | ARG | ARG |
| TRP | GLU | LYS | TRP | GLU | LEU | ASP | LEUASP | ILE | LYS | GLU | VAL | PHE | VAL | HIS |
| PRO | ASN | TYR | SER | LYS | SER | THR | THRASP | ASN | ASP | ILE | ALA | LEU | LEU | HIS |
| LEU | ALA | GLN | PRO | ALA | THR | LEU | SERGLN | THR | ILE | VAL | PRO | ILE | CYS | LEU |
| PRO | ASP | SER | GLY | LEU | ALA | GLU | ARG GLU | LEU | ASN | GLN | ALA | GLY | GLN | GLU |
| THR | LEU | VAL | THR | GLY | TRP | GLY | TYRHIS | SER | SER | ARG | GLU | LYS | GLU | ALA |
| LYS | ARG | GLN | ARG | THR | PHE | VAL | LEUASN | PHE | ILE | LYS | ILE | PRO | VAL | VAL |
| PRO | HIS | ASN | GLU | CYS | SER | GLU | VALMET | SER | ASN | MET | VAL | SER | GLU | ASN |
| MET | LEU | CYS | ALA | GLY | ILE | LEU | GLYASP | ARG | GLN | ASP | ALA | CYS | GLU | GLY |
| ASP | SER | GLY | GLY | PRO | MET | VAL | ALASER | PHE | HIS | GLY | THR | TRP | PHE | LEU |
| VAL | GLY | LEU | VAL | SER | TRP | GLY | GLUGLY | CYS | GLY | LEU | LEU | HIS | ASN | TYR |
| GLY | VAL | TYR | THR | LYS | VAL | SER | ARG TYR | LEU | ASP | TRP | ILE | HIS | GLY | HIS |
| ILE | ARG | ASP | LYS | GLU | ALA | PRO | GLNLYS | SER | TRP | ALA | PRO—COOH; and | | | |

(ii) a promoter positioned to drive expression of said DNA sequence;

(B) culturing said host cell transformed in step (A) under conditions suitable for expression of said DNA sequence; and (C) recovering said protein C zymogen from said culture.

3. A zymogen form of human protein C wherein the amino acid residue sequence comprises:

METTRPGLNLEUTHRSERLEULEULEU
PHEVALALATHRTRPGLYILESERGLY
THRPROALAPROLEUASPSERVALPHE
SERSERSERGLUARGALAHISGLNVAL
LEUARGILEARGLYSARGALAASNSER
PHELEUGLUGLULEUARGHISSERSER
LEUGLUARGGLUCYSILEGLUGLUILE
CYSASPPHEGLUGLUALALYSGLUILE
PHEGLNASNVALASPASPTHRLEUALA
PHETRPSERLYSHISVALASPGLYASP
GLNCYSLEUVALLEUPROLEUGLUHIS
PROCYSALASERLEUCYSCYSGLYHIS
GLYTHRCYSILEASPGLYILEGLYSER
PHESERCYSASPCYSARGSERGLYTRP
GLUGLYARGPHECYSGLNARGGLUVAL
SERPHELEUASNCYSSERLEUASPASN
GLYGLYCYSTHRHISTYRCYSLEUGLU
GLUVALGLYTRPARGARGCYSSERCYS
ALAPROGLYTYRLYSLEUGLYASPASP
LEULEUGLNCYSHISPROALAVALLYS
PHEPROCYSGLYARGPROTRPLYSARG
METGLULYSLYSARGSERHISLEULYS
ARGASPTHRGLUASPGLNGLUASPGLN
VALASPPROARGLEUILEASPGLYLYS
METTHRARGARGGLYASPSERPROTRP
GLNVALVALLEUILEUASPSERLYSLYS
LYSLEUALACYSGLYALAVALLEUILE
HISPROSERTRPVALLEUTHRALAALA
HISCYSMETASPGLUSERLYSLYSLEU
LEUVALARGLEUGLYGLUTYRASPLEU
ARGARGTRPGLULYSTRPGLULEUASP
LEUASPILELYSGLUVALPHEVALHIS
PROASNTYRSERLYSSERTHRTHRASP
ASNASPILEALALEULEUHISLEUALA

-continued

GLNPROALATHRLEUSERGLNTHRILE
VALPROILECYSLEUPROASPSERGLY
LEUALAGLUARGGLULEUASNGLNALA
GLYGLNGLUTHRLEUVALTHRGLYTRP
GLYTYRHISSERSERARGGLULYSGLU
ALALYSARGGLNARGTHRPHEVALLEU
ASNPHEILELYSILEPROVALVALPRO
HISASNGLUCYSSERGLUVALMETSER
ASNMETVALSERGLUASNMETLEUCYS
ALAGLYILELEUGLYASPARGGLNASP
ALACYSGLUGLYASPSERGLYGLYPRO
METVALALASERPHEHISGLYTHRTRP
PHELEUVALGLYLEUVALSERTRPGLY
GLUGLYCYSGLYLEULEUHISASNTYR
GLYVALTYRTHRLYSVALSERARGTYR
LEUASPTRPILEHISGLYHISILEARG
ASPLYSGLUALAPROGLNLYSSERTRP
ALAPRO—COOH.

4. A recombinant DNA expression vector comprising the DNA compound of claim 1.

5. The vector of claim 4 that is plasmid pLPC-Q313.

6. The vector of claim 4 that is plasmid pGT-Q313-h.

7. A eukaryotic host cell transformed with a vector of claim 4.

8. The eukaryotic host cell of claim 7 that is 293/pLPC-Q313.

9. The eukaryotic host cell of claim 8 that is 293/pGT-Q313-h.

10. The method of claim 2 wherein said recombinant DNA expression vector is plasmid pLPC-Q313.

11. The method of claim 2 wherein said recombinant DNA expression vector is plasmid pGT-Q313-h.

12. The method of claim 2 wherein sad host cell is selected from the group consisting of 293 and AV12 host cells.

13. A method of treating a disease state involving intravascular coagulation that comprises administering an activated zymogen form of human protein C produced by the method of claim 2.

14. The method of claim 13, wherein said disease state is selected from the group consisting of deep vein thrombosis, pulmonary embolism, peripheral arterial thrombosis, emboli originating from the heart or peripheral arteries, acute myocardial infarction, thrombotic strokes, and disseminated intravascular coagulation.

* * * * *

UNITED STATES PATENT AND TRADEMARK OFFICE
CERTIFICATE OF CORRECTION

PATENT NO.    : 5,460,953

DATED         : October 24, 1995

INVENTOR(S)   : Bruce E. Gerlitz
                Brian W. Grinnell

It is certified that an error appears in the above-identified patent and that said Letters Patent is hereby corrected as shown below:

Column 28, line 60, delete the word "sad", insert the word --said--.

Signed and Sealed this

Nineteenth Day of November, 1996

*Attest:*

BRUCE LEHMAN

*Attesting Officer*  *Commissioner of Patents and Trademarks*